(12) United States Patent
Watanabe et al.

(10) Patent No.: US 7,256,199 B1
(45) Date of Patent: Aug. 14, 2007

(54) PYRIMIDONE DERIVATIVES

(75) Inventors: Kazutoshi Watanabe, Kanagawa (JP);
Ryoichi Ando, Kanagawa (JP);
Ken-ichi Saito, Kanagawa (JP); Rie Kawamoto, Kanagawa (JP); Aya Shoda, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/787,426

(22) PCT Filed: Sep. 24, 1999

(86) PCT No.: PCT/JP99/05224

§ 371 (c)(1),
(2), (4) Date: Jul. 2, 2001

(87) PCT Pub. No.: WO00/18758

PCT Pub. Date: Apr. 6, 2001

(30) Foreign Application Priority Data

Sep. 25, 1998 (JP) .................................. 10-271277
Oct. 27, 1998 (JP) .................................. 10-305266

(51) Int. Cl.
C07D 401/04 (2006.01)
A61K 31/506 (2006.01)

(52) U.S. Cl. .................. 514/272; 544/320; 544/321

(58) Field of Classification Search ................ 514/269, 514/227.8, 235.8, 249, 255, 275, 272; 544/60, 544/123, 238, 295, 296, 297, 319, 320, 321, 544/326, 328, 298

See application file for complete search history.

(56) References Cited

U.S. PATENT DOCUMENTS

| | | | |
|---|---|---|---|
| 4,166,180 A | | 8/1979 | Kato et al. |
| 4,507,302 A | * | 3/1985 | Fast et al. .................. 514/272 |
| 4,619,933 A | * | 10/1986 | Stringfellow et al. ....... 514/272 |
| 4,725,600 A | | 2/1988 | Takaya et al. ............... 514/269 |
| 5,612,286 A | | 3/1997 | Mayer et al. |
| 6,096,753 A | * | 8/2000 | Spohr et al. ................ 514/269 |
| 6,107,301 A | * | 8/2000 | Aldrich et al. ............ 514/261.1 |
| 6,410,729 B1 | * | 6/2002 | Spohr et al. ................ 544/320 |
| 6,420,385 B1 | | 7/2002 | Spohr et al. |
| 6,586,441 B2 | * | 7/2003 | Borroni et al. ............. 514/275 |
| 6,844,335 B2 | * | 1/2005 | Garcia et al. .......... 514/211.15 |
| 2003/0187004 A1 | * | 10/2003 | Garcia et al. .............. 514/269 |
| 2005/0090490 A1 | | 4/2005 | Uehara et al. |
| 2005/0130967 A1 | | 6/2005 | Uehara et al. |
| 2005/0130998 A1 | * | 6/2005 | Carcia et al. .............. 514/269 |
| 2006/0252768 A1 | | 11/2006 | Watanabe et al. |

FOREIGN PATENT DOCUMENTS

| | | |
|---|---|---|
| EP | 0168262 | 1/1986 |
| EP | 0354179 | 7/1989 |
| EP | 1136482 | 9/2001 |
| HU | 218974 | 8/1995 |
| HU | P001698 | 4/2001 |
| JP | 49-035631 | 4/1974 |
| JP | 49-35632 | 4/1974 |
| JP | 49-035633 | 4/1974 |
| JP | 49-35634 | 4/1974 |
| JP | 49-035631 | * 9/1974 |
| JP | 49-035633 | * 9/1974 |
| JP | 52-71481 | 6/1977 |
| JP | 52/139085 | 11/1977 |
| JP | 6-239893 | 8/1994 |
| JP | 6-329551 | 11/1994 |
| WO | 93/11231 | 6/1993 |
| WO | 98/24782 | 6/1998 |
| WO | WO-98/24780 | * 6/1998 |
| WO | 01/070728 | 9/2001 |
| WO | 01/070729 | 9/2001 |
| WO | 03/027080 | 4/2003 |
| WO | 03/037888 | 5/2003 |
| WO | 2004/055007 | 7/2004 |
| WO | 2004/085408 | 10/2004 |

OTHER PUBLICATIONS

Ram, Vishnu J., "Chemotherapeutic agents . . . ", Chemical Abstract, 1992, vol. 116, Abstract #59167.*
Buehler et. al., "Pyrimidines series . . . ", Chemical Abstract 1966, vol. 65, Abstract #90645.*
Skulnick, H.I. et.al., "Pyrimidinones, . . . Interferon-Inducing Antviral Agents", 1985, vol. 28, pp. 1864-1869.*

(Continued)

*Primary Examiner*—Deepak Rao
(74) *Attorney, Agent, or Firm*—Greenblum & Bernstein, P.L.C.

(57) ABSTRACT

A pyrimidone derivative represented by the formula (I) or a salts thereof:

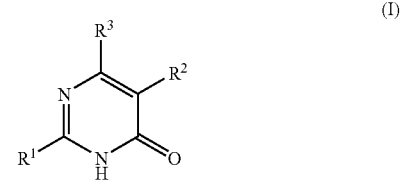

(I)

wherein $R^1$ represents an alkyl group, an alkenyl group, an alkynyl group, a cycloalkyl group, an aryl group and the like; $R^2$ represents a hydrogen atom, hydroxyl group, an alkyl group, an alkenyl group and the like, $R^3$ represents a pyridyl group, and a medicament comprising said derivative or a salt thereof as an active ingredient which is used for preventive and/or therapeutic treatment of a disease caused by tau protein kinase 1 hyperactivity such as Alzheimer disease.

14 Claims, No Drawings

OTHER PUBLICATIONS

Skulnick, H.I. et al., "Pyrimidinones, . . . Interferon-Inducing Antiviral Agents", 1985, vol. 28, pp. 1864-1869.*
Ulrich, Chapter 4: Crystallization, Kirk-Othmer Encyclopedia of Chemical Technology, Aug. 2002.*
Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
Tani et al., CAPLUS Abstract 84:44112, 1976.*
English Language Abstract of JP 6-239893, 1994.
English Language Abstract of JP 6-329551, 1994.
English Language Abstract of JP 52-71481, 1977.
Chemical Abstracts, vol. 100, No. 28, 1984, Columbus, Ohio, US, Abstract No. 174768e, M.R. Brana et al., "Reaction of N-(1-Oxido-4-Pyridylmethyl)-3,5-Dimethylbenzamide with Malononitrile in Acetic Anhydride", p. 627; XP002127059.
Chemical Abstracts, vol. 84, No. 7, 1976, Columbus, Ohio, US, Abstract No. 44112b, Tani et al., "4-Hydroxy-Pyridylpyrimidine Derivatives", p. 502, XP002127060.
Chemical Abstracts, vol. 82, No. 28, 1975, Columbus, Ohio, US, Abstract No. 170128n, Tani et al., "2,4,5-Trisubstituted-6-Pyridylpyrimidine Derivatives", p. 555, XP002127061.
Chemical Abstracts, vol. 83, No. 28, 1975, Columbus, Ohio, US, Abstract No. 10127z, Tani et al., "5-Nitro-6-Pyridylpyrimidine Derivatives", p. 853, XP002127062.
C.M. Wischik et al., "Isolation of a Fragment of Tau Derived from the core of the Paired Helical Filament of Alzheimer Disease", Proc. Natl. Acad. Sci. USA, vol. 85, pp. 4506-4510 (1988).
Inge Grundke-Iqbal et al., "Abnormal Phosphorylation of the Microtubule-Associated Protien τ (Tau) in Alzheimer Cytoskeletal Pathology", Proc. Natl. Acad. Sci. USA, vol. 83, pp. 4913-4917 (1986).
Koichi Ishiguro et al., "Tau Protein Kinase I Converts Normal Tau Protein into A68-like Component of Paired Helical Filaments", The Journal of Biological Chemistry, vol. 267, No. 15, pp. 10897-10901 (1992).
Bruce A. Yankner et al., "Neurotrophic and Neurotoxic Effects of Amyloid β Protein: Reversal by Tachykinin Neuropeptides", Science, vol. 250, pp. 279-282 (1990).
Akihiko Takashima et al., "Tau Protein Kinase I is Essential for Amyloid β-Protein-Induced Neurotoxicity", Proc. Natl. Acad. Sci. USA, vol. 90, pp. 7789-7793 (1993).
Von Hans-Joachim Kabbe, "Substituierte 4-Hydroxy- und 4-Amino-Pyrimidine", Liebigs. Ann. Chem., vol. 701, pp. 144-149 (1967).
Harvey I. Skulnick et al., "Pyrimidinones. 1. 2-Amino-5-Halo-6-Aryl-4(3H)-Pyrimidinones. Interferon- Inducing Antiviral Agents", J. Med. Chem., vol. 28, pp. 1864-1869 (1985).
G. Glenner et al., Biochemical and Biophysical Research Communications, vol. 120, No. 3, 1984, pp. 885-890.
C.L. Masters et al., The EMBO Journal, vol. 4, No. 11, 1985, pp. 2757-2763.
C.L. Masters et al., Proc. Natl. Acad. Sci. USA, vol. 82, Jun. 1985, pp. 4245-4249.
J. Kondo et al., Neuron, vol. 1, Nov. 1988, pp. 827-834.
R. Sherrington et al., Nature, vol. 375, Jun. 29, 1995, pp. 754-760.
E. Levy-Lahad et al., Science, vol. 269, Aug. 18, 1995, pp. 973-977.
E.I. Rogaev et al., Nature, vol. 376, Aug. 31, 1995, pp. 775-778.
D.R. Borchelt et al., Neuron, vol. 17, Nov. 1996, pp. 1005-1013.
T. Tomita et al., Proc. Natl. Acad. Sci. USA, vol. 94, Mar. 1997, pp. 2025-2030.
Sai-Shin Igaku, vol. 49, No. 9, 1994, pp. 1506-1512.
D.W. Dickson et al., Society for Neuroscience Abstracts, vol. 17, 1991, pp. 1445.
R. Siman et al., The Journal of Neuroscience, vol. 10, No. 7, Jul. 1990, pp. 2400-2411.
Shin-kei Shinpo, vol. 34, 1990, pp. 343-349.
Tanpaku-shitu Kaku-san Koso, vol. 41, 1996, pp. 1476-1483.
Tanpaku-shitu Kaku-san Koso, vol. 36, 1991, pp. 2-11.
Igaku no Ayumi, vol. 158, No. 9, Aug. 31, 1991, pp. 511-514.
Y. Ihara et al., J. Biochem., vol. 99, 1986, pp. 1807-1810.
I. Grundke-Iqbal et al., Proc. Natl. Acad. Sci. USA, vol. 83, Jul. 1986, pp. 4913-4917.
Seikagaku, vol. 64, No. 5, pp. 308-312.
K. Ishiguro et al., FEBS Lett., vol. 325, Jul. 1993, pp. 167-172.
H. Yinglin, Tetrahedron Letters, vol. 30, No. 39, 1989, pp. 5285-5286.
H. Yinglin, Synthesis, pp. 122-124, Feb. 1990.
R.L. Duncan Jr. et al., J. Med. Chem., vol. 13, No. 1, Jan. 1970, pp. 1-6.
D.L. Thai et al., J. Med. Chem., vol. 41, 1998, pp. 591-601.
Chemical Abstract 1992, vol. 116, Abstract # 59167.
Chemical Abstract 1966, vol. 65, Abstract # 90645.
U.S. Appl. No. 10/489,606 to Uehara et al., filed Sep. 20, 2002.
U.S. Appl. No. 10/489,607 to Uehara et al., filed Sep. 20, 2002.
Von Hans-Joachim Kabbe, "Substituierte 4-Hydroxy- und 4-Amino-Pyrimidine", Liebigs. Ann. Chem., vol. 704, pp. 144-149 (1967).
U.S. Appl. No. 10/538,766, filed Dec. 12, 2003 to USUI et al.

* cited by examiner

PYRIMIDONE DERIVATIVES

TECHNICAL FIELD

The present invention relates to compounds that are useful as an active ingredient of a medicament for preventive and/or therapeutic treatment of diseases caused by abnormal advance of tau protein kinase 1, such as Alzheimer disease and the like.

BACKGROUND ART

Alzheimer disease is progressive senile dementia, in which marked cerebral cortical atrophy is observed due to degeneration of nerve cells and decrease of nerve cell number. Pathologically, numerous senile plaques and neurofibrillary tangles are observed in brain. The number of patients has been increased with the increment of aged population, and the disease arises a serious social problem. Although various theories have been proposed, a cause of the disease has not yet been elucidated. Early resolution of the cause has been desired.

It has been known that the degree of appearance of two characteristic pathological changes of Alzheimer disease well correlates to the degree of intellectual dysfunction. Therefore, researches have been conducted from early 1980's to reveal the cause of the disease through molecular level investigations of components of the two pathological changes. Senile plaques accumulate extracellularly, and amyloid β protein has been elucidated as their main component (abbreviated as "Aβ" hereinafter in the specification: Biochem. Biophys. Res. Commun., 120, 885 (1984): EMBO J., 4, 2757 (1985); Proc. Natl. Acad. Sci. USA, 82, 4245 (1985)). In the other pathological change, i.e., the neurofibrillary tangles, a double-helical filamentous substance called paired helical filament (abbreviated as "PHF" hereinafter in the specification) accumulate intracellularly, and tau protein, which is a kind of microtubule-associated protein specific for brain, has been revealed as its main component (Proc. Natl. Acad. Sci. USA, 85, 4506 (1988); Neuron, 1, 827 (1988)).

Furthermore, on the basis of genetic investigations, presenilins 1 and 2 were found as causative genes of familial Alzheimer disease (Nature, 375, 754 (1995); Science, 269, 973 (1995); Nature, 376, 775 (1995)), and it has been revealed that presence of mutants of presenilins 1 and 2 promotes the secretion of Aβ (Neuron, 17, 1005 (1996); Proc. Natl. Acad. Sci. USA, 94, 2025 (1997)). From these results, it is considered that, in Alzheimer disease, Aβ abnormally accumulates and agglomerates due to a certain reason, which engages with the formation of PHF to cause death of nerve cells. It is also expected that extracellular outflow of glutamic acid and activation of glutamate receptor responding to the outflow may possibly be important factors in an early process of the nerve cell death caused by ischemic cerebrovascular accidents (Sai-shin Igaku [Latest Medicine], 49, 1506 (1994)).

It has been reported that kainic acid treatment that stimulates the AMPA receptor, one of glutamate receptor, increases mRNA of the amyloid precursor protein (abbreviated as "APP" hereinafter in the specification) as a precursor of Aβ (Society for Neuroscience Abstracts, 17, 1445 (1991)), and also promotes metabolism of APP (The Journal of Neuroscience, 10, 2400 (1990)). Therefore, it has been strongly suggested that the accumulation of Aβ is involved in cellular death due to ischemic cerebrovascular disorders. Other diseases in which abnormal accumulation and agglomeration of Aβ are observed include, for example, Down syndrome, cerebral bleeding due to solitary cerebral amyloid angiopathy, Lewy body disease (Shin-kei Shinpo [Nerve Advance], 34, 343 (1990); Tanpaku-shitu Kaku-san Koso [Protein, Nucleic Acid, Enzyme], 41, 1476 (1996)) and the like. Furthermore, as diseases showing neurofibrillary tangles due to the PHF accumulation, examples include progressive supranuclear palsy, subacute sclerosing panencephalitic parkinsonism, postencephalitic parkinsonism, pugilistic encephalitis, Guam parkinsonism-dementia complex, Lewy body disease and the like (Tanpakushitu Kakusan Koso [Protein, Nucleic Acid, Enzyme], 36, 2 (1991); Igaku no Ayumi [Progress of Medicine], 158, 511 (1991); Tanpakushitu Kakusan Koso [Protein, Nucleic Acid, Enzyme], 41, 1476 (1996)).

The tau protein is generally composed of a group of related proteins that forms several bands at molecular weights of 48–65 kDa in SDS-polyacrylamide gel electrophoresis, and it promotes the formation of microtubules. It has been verified that tau protein incorporated in the PHF in the brain suffering from Alzheimer disease is abnormally phosphorylated compared with usual tau protein (J. Biochem., 99, 1807 (1986); Proc. Natl. Acad. Sci. USA, 83, 4913 (1986)). An enzyme catalyzing the abnormal phosphorylation has been isolated. The protein was named as tau protein kinase 1 (abbreviated as "TPK1" hereinafter in the specification), and its physicochemical properties have been elucidated (Seikagaku [Biochemistry], 64, 308 (1992); J. Biol. Chem., 267, 10897 (1992)). Moreover, cDNA of rat TPK1 was cloned from a rat cerebral cortex cDNA library based on a partial amino acid sequence of TPK1, and its nucleotide sequence was determined and an amino acid sequence was deduced (Japanese Patent Un-examined Publication [Kokai] No. 6-239893/1994). As a result, it has been revealed that the primary structure of the rat TPK1 corresponds to that of the enzyme known as rat GSK-3 β (glycogen synthase kinase 3β, FEBS Lett., 325, 167 (1993)).

It has been reported that Aβ, the main component of senile plaques, is neurotoxic (Science, 250, 279 (1990)). However, various theories have been proposed as for the reason why Aβ causes the cell death, and any authentic theory has not yet been established. Takashima et al. observed that the cell death was caused by Aβ treatment of fetal rat hippocampus primary culture system, and then found that the TPK1 activity was increased by Aβ treatment and the cell death by Aβ was inhibited by antisense of TPK1 (Proc. Natl. Acad. Sci. USA, 90, 7789 (1993); Japanese Patent Un-examined Publication [Kokai] No. 6-329551/1994).

In view of the foregoing, compounds which inhibit the TPK1 activity may possibly suppress the neurotoxicity of Aβ and the formation of PHF and inhibit the nerve cell death in the Alzheimer disease, thereby cease or defer the progress of the disease. The compounds may also be possibly used as a medicament for therapeutic treatment of ischemic cerebrovascular disorder, Down syndrome, cerebral amyloid angiopathy, cerebral bleeding due to Lewy body disease and the like by suppressing the cytotoxicity of Aβ. Furthermore, the compounds may possibly be used as a medicament for therapeutic treatment of neurodegenerative diseases such as progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration and frontotemporal dementia.

As structurally similar compounds to the compounds of the present invention represented by formula (I) described later, compounds represented by the following formula (A) are known:

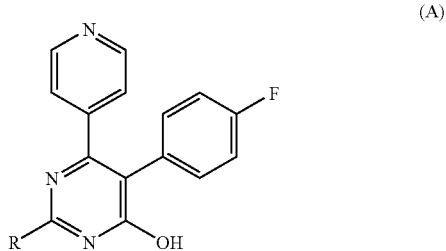

wherein R represents 2,6-dichlorobenzyl group, 2-(2-chlorophenyl)ethylamino group, 3-phenylpropylamino group, or 1-methyl-3-phenylpropylamino group (WO98/24782). The compounds represented by formula (A) are characterized to have 4-fluorophenyl group at the 5-position of the pyrimidine ring, and not falling within the scope of the present invention. Moreover, main pharmacological activity of the compounds represented by formula (A) is anti-inflammatory effect, whereas the compounds of the present invention represented by formula (I) are useful as a TPK1 inhibitor or a medicament for therapeutic treatment of neurodegenerative diseases, and therefore, their pharmacological activities are totally different to each other.

DISCLOSURE OF THE INVENTION

An object of the present invention is to provide compounds useful as an active ingredient of a medicament for preventive and/or therapeutic treatment of diseases such as Alzheimer disease and the like. More specifically, the object is to provide novel compounds useful as an active ingredient of a medicament that enables radical prevention and/or treatment of the diseases such as Alzheimer disease by inhibiting the TPK1 activity to suppress the neurotoxicity of Aβ and the formation of the PHF and by inhibiting the drop of nerve cells.

In order to achieve the foregoing object, the inventors of the present invention conducted screenings of various compounds having inhibitory activity against the phosphorylation of TPK1. As a result, they found that compounds represented by the following formula (I) had the desired activity and were useful as an active ingredient of a medicament for preventive and/or therapeutic treatment of the aforementioned diseases. The present invention was achieved on the basis of these findings.

The present invention thus provides pyrimidone derivatives represented by formula (I) or salts thereof, solvates thereof or hydrates thereof:

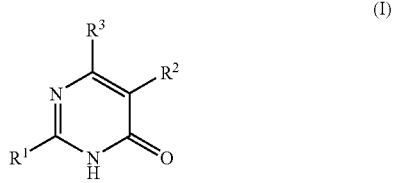

wherein $R^1$ represents a $C_1$–$C_{18}$ alkyl group which may be substituted, a $C_3$–$C_{18}$ alkenyl group which may be substituted, a $C_3$–$C_{18}$ alkynyl group which may be substituted, a $C_3$–$C_8$ cycloalkyl group which may be substituted, a $C_6$–$C_{14}$ aryl group which may be substituted, a $C_1$–$C_{18}$ alkyloxy group which may be substituted, a $C_3$–$C_{18}$ alkenyloxy group which may be substituted, a $C_3$–$C_{18}$ alkynyloxy group which may be substituted, a $C_3$–$C_8$ cycloalkyloxy group which may be substituted, a $C_6$–$C_{14}$ aryloxy group which may be substituted, a heterocyclic group which may be substituted, or a group represented by —N($R^4$)—W—$R^5$ wherein $R^4$ and $R^5$ independently represent a hydrogen atom, a $C_1$–$C_{18}$ alkyl group which may be substituted, a $C_3$–$C_{18}$ alkenyl group which may be substituted, a $C_3$–$C_{18}$ alkynyl group which may be substituted, a $C_3$–$C_8$ cycloalkyl group which may be substituted, or a $C_6$–$C_{14}$ aryl group which may be substituted, and symbol "W" represents a single bond, carbonyl group, sulfonyl group, or a nitrogen atom which may be substituted with a $C_1$–$C_{18}$ alkyl group which may be substituted;

$R^2$ represents hydrogen atom, hydroxyl group, a $C_1$–$C_8$ alkyl group which may be substituted, a $C_3$–$C_8$ alkenyl group which may be substituted, a $C_3$–$C_8$ cycloalkyl group which may be substituted, a $C_1$–$C_8$ alkyloxy group which may be substituted, a $C_3$–$C_8$ cycloalkyloxy group which may be substituted, a $C_6$–$C_{14}$ aryloxy group which may be substituted, a $C_1$–$C_8$ alkylthio group which may be substituted, a halogen atom, nitro group, cyano group, an amino group which may be substituted, carboxyl group, a $C_1$–$C_8$ alkyloxycarbonyl group which may be substituted, a $C_3$–$C_8$ cycloalkyloxycarbonyl group which may be substituted, carbamoyl group, a $C_1$–$C_8$ alkylaminocarbonyl group which may be substituted, or a $C_1$–$C_8$ dialkylaminocarbonyl group which may be substituted; and $R^3$ represents a pyridyl group which may be substituted.

According to another aspect of the present invention, there is provided a medicament comprising as an active ingredient a substance selected from the group consisting of the pyrimidone derivatives represented by formula (I) and the physiologically acceptable salts thereof, and the solvates thereof and the hydrates thereof. As preferred embodiments of the medicament, there are provided the aforementioned medicament which is used for preventive and/or therapeutic treatment of diseases caused by tau protein kinase 1 hyperactivity, and the aforementioned medicament which is used for preventive and/or therapeutic treatment of neurodegenerative diseases. As further preferred embodiments of the present invention, there are provided the aforementioned medicament wherein the diseases are selected from the group consisting of Alzheimer disease, ischemic cerebrovascular accidents, Down syndrome, cerebral bleeding due to cerebral amyloid angiopathy, progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration and frontotemporal dementia; and the aforementioned medicament in the form of pharmaceutical composition containing the above substance as an active ingredient together with one or more pharmaceutical additives. The present invention further provides an inhibitor of tau protein kinase 1 comprising as an active ingredient a substance selected from the group consisting of the pyrimidone derivatives of formula (I) and the salts thereof, and the solvates thereof and the hydrates thereof.

According to further aspects of the present invention, there are provided a method for preventive and/or therapeutic treatment of diseases caused by tau protein kinase 1 hyperactivity, which comprises the step of administering to a patient a preventively and/or therapeutically effective amount of a substance selected from the group consisting of the pyrimidone derivatives of formula (I) and the physiologically acceptable salts thereof, and the solvates thereof and the hydrates thereof; and a use of a substance selected from the group consisting of the pyrimidone derivatives of formula (I) and the physiologically acceptable salts thereof, and the solvates thereof and the hydrates thereof for the manufacture of the aforementioned medicament.

The present invention is also directed to a method for therapeutic treatment of a disease caused by tau protein kinase 1 hyperactivity, which comprises administering to a patient a therapeutically effective amount of a substance selected from the group consisting of a pyrimidone derivative represented by formula (I) or a salt thereof, or a solvate thereof or a hydrate thereof:

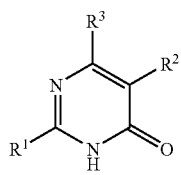

(I)

wherein
R$^1$ represents a group represented by —N(R$^4$)—W—R$^5$
wherein
R$^4$ and R$^5$ independently represent a hydrogen atom, a C$_1$–C$_{18}$ alkyl group which may be substituted, a C$_3$–C$_{18}$ alkenyl group which may be substituted, a C$_3$–C$_{18}$ alkynyl group which may be substituted, a C$_3$–C$_8$ cycloalkyl group which may be substituted, or a C$_6$–C$_{14}$ aryl group which may be substituted, and
symbol "W" represents a single bond, a carbonyl group, a sulfonyl group, or a nitrogen atom which may be substituted with a C$_1$–C$_{18}$ alkyl group which may be substituted;
R$^2$ represents a hydrogen atom, hydroxyl group, an unsubstituted C$_1$–C$_8$ alkyl group, a C$_3$–C$_8$ alkenyl group which may be substituted, a C$_3$–C$_8$ cycloalkyl group which may be substituted, a C$_1$–C$_8$ alkyloxy group which may be substituted, a C$_3$–C$_8$ cycloalkyloxy group which may be substituted, a C$_6$–C$_{14}$ aryloxy group which may be substituted, a C$_1$–C$_8$ alkylthio group which may be substituted, a halogen atom, nitro group, cyano group, an amino group which may be substituted, carboxyl group, a C$_1$–C$_8$ alkyloxycarbonyl group which may be substituted, a C$_3$–C$_8$ cycloalkyloxycarbonyl group which may be substituted, carbamoyl group, a C$_1$–C$_8$ alkylaminocarbonyl group which may be substituted, or a C$_1$–C$_8$ dialkylaminocarbonyl group which may be substituted; and
R$^3$ represents a pyridyl group which may be substituted.

The present invention is also directed to a method for prophylactic treatment of a disease caused by tau protein kinase 1 hyperactivity, which comprises administering to a patient a prophylactically effective amount of a substance selected from the group consisting of a pyrimidone derivative represented by formula (I) or a salt thereof, or a solvate thereof or a hydrate thereof:

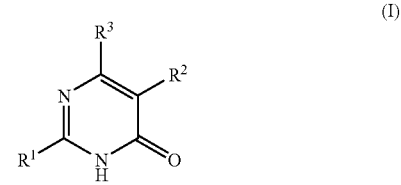

(I)

wherein
R$^1$ represents a group represented by —N(R$^4$)—W—R$^5$
wherein
R$^4$ and R$^5$ independently represent a hydrogen atom, a C$_1$–C$_{18}$ alkyl group which may be substituted, a C$_3$–C$_{18}$ alkenyl group which may be substituted, a C$_3$–C$_{18}$ alkynyl group which may be substituted, a C$_3$–C$_8$ cycloalkyl group which may be substituted, or a C$_6$–C$_{14}$ aryl group which may be substituted, and
symbol "W" represents a single bond, a carbonyl group, a sulfonyl group, or a nitrogen atom which may be substituted with a C$_1$–C$_{18}$ alkyl group which may be substituted;
R$^2$ represents a hydrogen atom, hydroxyl group, an unsubstituted C$_1$–C$_8$ alkyl group, a C$_3$–C$_8$ alkenyl group which may be substituted, a C$_3$–C$_8$ cycloalkyl group which may be substituted, a C$_1$–C$_8$ alkyloxy group which may be substituted, a C$_3$–C$_8$ cycloalkyloxy group which may be substituted, a C$_6$–C$_{14}$ aryloxy group which may be substituted, a C$_1$–C$_8$ alkylthio group which may be substituted, a halogen atom, nitro group, cyano group, an amino group which may be substituted, carboxyl group, a C$_1$–C$_8$ alkyloxycarbonyl group which may be substituted, a C$_3$–C$_8$ cycloalkyloxycarbonyl group which may be substituted, carbamoyl group, a C$_1$–C$_8$ alkylaminocarbonyl group which may be substituted, or a C$_1$–C$_8$ dialkylaminocarbonyl group which may be substituted; and
R$^3$ represents a pyridyl group which may be substituted.

The present invention is also directed to a method of inhibiting tau protein kinase 1 which comprises administering to a mammal a therapeutically effective amount of at least one pyrimidone derivative represented by formula (I) or a salt thereof, or a solvate thereof or a hydrate thereof

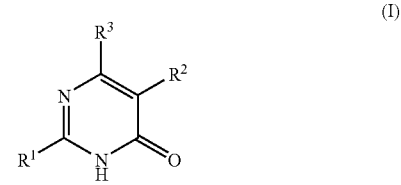

(I)

wherein
R$^1$ represents a group represented by —N(R$^4$)—W—R$^5$
wherein
R$^4$ and R$^5$ independently represent a hydrogen atom, a C$_1$–C$_{18}$ alkyl group which may be substituted, a C$_3$–C$_{18}$ alkenyl group which may be substituted, a C$_3$–C$_{18}$ alkynyl group which may be substituted, a C$_3$–C$_8$ cycloalkyl group which may be substituted, or a C$_6$–C$_{14}$ aryl group which may be substituted, and symbol "W" represents a single bond, a carbonyl group, a sulfonyl group, or a nitrogen atom which may be substituted with a C$_1$–C$_{18}$ alkyl group which may be substituted;

R$^2$ represents a hydrogen atom, hydroxyl group, an unsubstituted C$_1$–C$_8$ alkyl group, a C$_3$–C$_8$ alkenyl group which may be substituted, a C$_3$–C$_8$ cycloalkyl group which may be substituted, a C$_1$–C$_8$ alkyloxy group which may be substituted, a C$_3$–C$_8$ cycloalkyloxy group which may be substituted, a C$_6$–C$_{14}$ aryloxy group which may be substituted, a C$_1$–C$_8$ alkylthio group which may be substituted, a halogen atom, nitro group, cyano group, an amino group which may be substituted, carboxyl group, a C$_1$–C$_8$ alkyloxycarbonyl group which may be substituted, a C$_3$–C$_8$ cycloalkyloxycarbonyl group which may be substituted, carbamoyl group, a C$_1$–C$_8$ alkylaminocarbonyl group which may be substituted, or a C$_1$–C$_8$ dialkylaminocarbonyl group which may be substituted; and R$^3$ represents a pyridyl group which may be substituted.

The disease can be a neurodegenerative disease.

The disease can be selected from the group consisting of Alzheimer disease, ischemic cerebrovascular accidents, Down syndrome, cerebral bleeding due to cerebral amyloid angiopathy, progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration and frontotemporal dementia.

R$^2$ can represent a hydrogen atom and R$^3$ can represent a 4-pyridyl group which may be substituted.

R$^2$ can represent an unsubstituted, linear C$_1$–C$_8$ alkyl group.

The present invention is also directed to a pyrimidone derivative represented by formula (I) or a salt thereof, or a solvate thereof or a hydrate thereof:

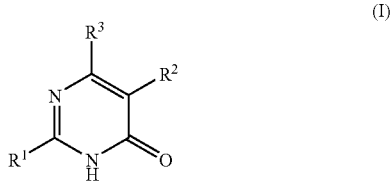

(I)

wherein
R$^1$ represents a group represented by —N(R$^4$)—W—R$^5$ wherein
R$^4$ represents a hydrogen atom;
R$^5$ represents a C$_1$–C$_{18}$ alkyl group which may be substituted, a C$_3$–C$_{18}$ alkenyl group which may be substituted, a C$_3$–C$_{18}$ alkynyl group which may be substituted, a C$_3$–C$_8$ cycloalkyl group which may be substituted, or a C$_6$–C$_{14}$ aryl group which may be substituted, and symbol "W" represents a single bond, a carbonyl group, a sulfonyl group, or a nitrogen atom which may be substituted with a C$_1$–C$_{18}$ alkyl group which may be substituted;

R$^2$ represents a hydrogen atom, hydroxyl group, an unsubstituted, linear C$_1$–C$_8$ alkyl group, a C$_3$–C$_8$ alkenyl group which may be substituted, a C$_3$–C$_8$ cycloalkyl group which may be substituted, a C$_1$–C$_8$ alkyloxy group which may be substituted, a C$_3$–C$_8$ cycloalkyloxy group which may be substituted, a C$_6$–C$_{14}$ aryloxy group which may be substituted, a C$_1$–C$_8$ alkylthio group which may be substituted, a halogen atom, nitro group, cyano group, an amino group which may be substituted, carboxyl group, a C$_1$–C$_8$ alkyloxycarbonyl group which may be substituted, a C$_3$–C$_8$ cycloalkyloxycarbonyl group which may be substituted, carbamoyl group, a C$_1$–C$_8$ alkylaminocarbonyl group which may be substituted, or a C$_1$–C$_8$ dialkylaminocarbonyl group which may be substituted; and R$^3$ represents a 4-pyridyl group which may be substituted.

The present invention is also directed to a pyrimidone derivative represented by formula (I) or a salt thereof, or a solvate thereof or a hydrate thereof:

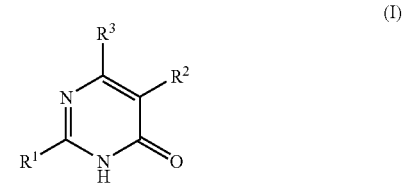

(I)

wherein R$^1$ represents a group represented by —N(R$^4$)—W—R$^5$ wherein
R$^4$ represents a hydrogen atom, a C$_1$–C$_{18}$ alkyl group which may be substituted, a C$_3$–C$_{18}$ alkenyl group which may be substituted, a C$_3$–C$_{18}$ alkynyl group which may be substituted, a C$_3$–C$_8$ cycloalkyl group which may be substituted, or a C$_6$–C$_{14}$ aryl group which may be substituted, R$^5$ represents an alkyl group which may be substituted, said alkyl group being one of ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, a linear or branched heptyl group, octyl group, nonyl group, decyl group, undecyl group, dodecyl group, tridecyl group, tetradecyl group, pentadecyl group or octadecyl group, a C$_3$–C$_{18}$ alkenyl group which may be substituted, a C$_3$–C$_{18}$ alkynyl group which may be substituted, a C$_3$–C$_8$ cycloalkyl group which may be substituted, or a C$_6$–C$_{14}$ aryl group which may be substituted, and symbol "W" represents a single bond, a carbonyl group, a sulfonyl group, or a nitrogen atom which may be substituted with a C$_1$–C$_{18}$ alkyl group which may be substituted;

R$^2$ represents a hydrogen atom, hydroxyl group, an unsubstituted, linear C$_1$–C$_8$ alkyl group, a C$_3$–C$_8$ alkenyl group which may be substituted, a C$_3$–C$_8$ cycloalkyl group which may be substituted, a C$_1$–C$_8$ alkyloxy group which may be substituted, a C$_3$–C$_8$ cycloalkyloxy group which may be substituted, a C$_6$–C$_{14}$ aryloxy group which may be substituted, a C$_1$–C$_8$ alkylthio group which may be substituted, a halogen atom, nitro group, cyano group, an amino group which may be substituted, carboxyl group, a C$_1$–C$_8$ alkyloxycarbonyl group which may be substituted, a C$_3$–C$_8$ cycloalkyloxycarbonyl group which may be substituted, carbamoyl group, a C$_1$–C$_8$ alkylaminocarbonyl group which may be substituted, or a $C_1$–$C_8$ dialkylaminocarbonyl group which may be substituted; and $R^3$ represents a 4-pyridyl group which may be substituted.

$R^5$ can represent a $C_1$–$C_{18}$ alkyl group substituted with a $C_6$–$C_{10}$ aryl.

$R^2$ can represent a hydrogen atom, an unsubstituted, linear $C_1$–$C_8$ alkyl group, or a halogen atom.

$R^2$ can represent a hydrogen atom.

The symbol "W" can represent a single bond or a carbonyl group.

$R^1$ can represent N,N-diethylamino group, N,N-dipropylamino group, N-benzyl-N-methylamino group, N-isobutyl-N-methylamino group, N-benzylamino group, N-(3-hydroxypropyl)amino group, N-cyclohexylmethylamino group, N-phenylamino group, N-(4-ethylphenyl)amino group, N-(3-bromophenyl)amino group or N-(3-methoxyphenyl) amino group.

$R^3$ can represent 4-pyridyl group.

The pyrimidone derivative can be selected from the group of:

2-(N-phenylamino)-6-(4-pyridyl)pyrimidin-4-one,
2-(N,N-diethylamino)-6-(4-pyridyl)pyrimidin-4-one,
2-(N,N-dipropylamino)-6-(4-pyridyl)pyrimidin-4-one,
2-(N-benzylamino)-6-(4-pyridyl)pyrimidin-4-one,
2-(N-benzyl-N-methylamino)-6-(4-pyridyl)pyrimidin-4-one,
2-(N-(3-bromophenyl)amino)-6-(4-pyridyl)pyrimidin-4-one,
2-(N-(4-ethylphenyl)amino)-6-(4-pyridyl)pyrimidin-4-one,
2-(N-(3-methoxyphenyl)amino)-6-(4-pyridyl)pyrimidin-4-one,
2-(N-cyclohexylmethylamino)-6-(4-pyridyl)pyrimidin-4-one, and
2-(N-isobutyl-N-methylamino)-6-(4-pyridyl)pyrimidin-4-one, or a salt thereof, or a solvate thereof or a hydrate thereof.

The present invention is also directed to a pharmaceutical composition comprising as an active ingredient a substance selected from the group consisting of the pyrimidone derivatives or a salt thereof, or a solvate thereof or a hydrate thereof according to any of the above.

BEST MODE FOR CARRYING OUT THE INVENTION

The "alkyl group" or an alkyl portion of a functional group containing the alkyl portion (alkoxyl group, for example) used herein may be either linear or branched. The $C_1$–$C_{18}$ alkyl group represented by $R^1$ may be, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, or a linear or branched heptyl group, octyl group, nonyl group, decyl group, undecyl group, dodecyl group, tridecyl group, tetradecyl group, pentadecyl group or octadecyl group. In the specification, when a functional group is defined as "which may be substituted" or "optionally substituted", the number of substituents as well as their types and substituting positions are not particularly limited, and when two or more substituents are present, they may be the same or different.

When the $C_1$–$C_{18}$ alkyl group represented by $R^1$ has one or more substituents A, the alkyl group may have one or more substituents A selected form the group consisting of a $C_3$–$C_8$ cycloalkyl group such as cyclopropyl group, cyclobutyl group, cyclopentyl group, cyclohexyl group, cycloheptyl group, and cyclooctyl group; a $C_6$–$C_{10}$ aryl group such as phenyl group, 1-naphthyl group, and 2-naphthyl group; a $C_3$–$C_8$ cycloalkyloxy group such as cyclopropyloxy group, cyclobutyloxy group, cyclopentyloxy group, cyclohexyloxy group, cycloheptyloxy group, and cyclooctyloxy group; fluorenyl group; a $C_1$–$C_5$ alkoxyl group such as methoxy group, ethoxy group, propoxy group, isopropoxy group, butoxy group, isobutoxy group, tert-butoxy group, pentyloxy group, and isopentyloxy group; a $C_6$–$C_{14}$ aryloxy group such as phenoxy group, and naphthoxy group; a $C_1$–$C_5$ alkylthio group such as methylthio group, ethylthio group, propylthio group, butylthio group, and pentylthio group; a $C_6$–$C_{14}$ arylthio group such as phenylthio group, and naphthylthio group; a $C_1$–$C_5$ alkylsulfonyl group such as methanesulfonyl group, ethanesulfonyl group, propanesulfonyl group, butanesulfonyl group, and pentanesulfonyl group; a $C_6$–$C_{14}$ arylsulfonyl group such as phenylsulfonyl group, and naphthylsulfonyl group; a halogen atom such as fluorine atom, chlorine atom, bromine atom, and iodine atom; a $C_1$–$C_5$ halogenated alkyl group such as trifluoromethyl group; hydroxyl group; nitro group; oxo group; formyl group; a $C_2$–$C_6$ alkylcarbonyl group such as acetyl group, propionyl group, butyryl group, and valeryl group; amino group; a $C_1$–$C_5$ monoalkylamino group such as methylamino group, ethylamino group, propylamino group, isopropylamino group, butylamino group, isobutylamino group, tert-butylamino group, pentylamino group, and isopentylamino group; a $C_2$–$C_{10}$ dialkylamino group such as dimethylamino group, ethylmethylamino group, diethylamino group, methylpropylamino group, and diisopropylamino group; and a residue of heterocyclic ring having 1–4 hetero atoms selected from oxygen atom, sulfur atom, and nitrogen atom, and having total ring-constituting atoms of 5–10, for example, furan ring, dihydrofuran ring, tetrahydrofuran ring, pyran ring, dihydropyran ring, tetrahydropyran ring, benzofuran ring, isobenzofuran ring, chromene ring, chroman ring, isochroman ring, thiophene ring, benzothiophene ring, pyrrole ring, pyrroline ring, pyrrolidine ring, imidazole ring, imidazoline ring, imidazolidine ring, pyrazole ring, pyrazoline ring, pyrazolidine ring, triazole ring, tetrazole ring, pyridine ring, pyridine oxide ring, piperidine ring, pyrazine ring, piperazine ring, pyrimidine ring, pyridazine ring, indolizine ring, indole ring, indoline ring, isoindole ring, isoindoline ring, indazole ring, benzimidazole ring, purine ring, quinolizine ring, quinoline ring, phthalazine ring, naphtylidine ring, quinoxaline ring, quinazoline ring, cinnoline ring, pteridine ring, oxazole ring, oxazolidine ring, isoxazole ring, isoxazolidine ring, thiazole ring, benzothiazole ring, thiazylidine ring, isothiazole ring, isothiazolidine ring, dioxane ring, dithian ring, morpholine ring, thiomorpholine ring, phthalimide ring and the like.

When an aryl group or a heterocyclic group is present as a substituent, the group may have one or more substituents B selected form the group consisting of a $C_1$–$C_{18}$ alkyl group such as methyl group, ethyl group, propyl group, isopropyl group, butyl group, isobutyl group, sec-butyl group, tert-butyl group, pentyl group, isopentyl group, neopentyl group, 1,1-dimethylpropyl group, hexyl group, isohexyl group, heptyl group, octyl group, nonyl group, decyl group, undecyl group, dodecyl group, tridecyl group, tetradecyl group, pentadecyl group, and octadecyl group, and the aforementioned substituent A.

Examples of the $C_3$–$C_{18}$ alkenyl group represented by $R^1$ include, for example, allyl group, 2-butenyl group, 3-butenyl group, 2-pentenyl group, 3-pentenyl group, 4-pentenyl group, 2-methyl-2-butenyl group, 3-methyl-2-butenyl group, 2-hexenyl group, 5-hexenyl group, 2-heptenyl group, 6-heptenyl group, 2-octenyl group, 7-octenyl group, 2-nonenyl group, 8-nonenyl group and the like, and examples of the $C_3$–$C_{18}$ alkynyl group represented by $R^1$ include, for example, propargyl group, 2-butynyl group, 3-butynyl group, 2-pentynyl group, 3-pentynyl group, 4-pentynyl group, 1-methyl-2-pentynyl group, 4-methyl-2-pentynyl group, 2-hexynyl group, 5-hexynyl group, 2-heptynyl group, 6-heptynyl group, 2-octynyl group, 7-octynyl group and the like. These groups may be substituted with one or more substituents A.

Examples of the $C_3$–$C_8$ cycloalkyl group represented by $R^1$ include, for example, cyclopropyl group, cyclobutyl group, cyclopentyl group, cyclohexyl group, cycloheptyl group, cyclooctyl group and the like, and examples of the $C_6$–$C_{14}$ aryl group represented by $R^1$ include, for example, phenyl group, naphthyl group, anthryl group and the like. These groups may be substituted with one or more substituents B. The $C_6$–$C_{14}$ aryl group represented by $R^1$ may further have one or more substituents selected from the group consisting of a hydroxyalkyl group such as hydroxymethyl group, 1-hydroxyethyl group, 2-hydroxyethyl group, and 3-hydroxypropyl group; a $C_1$–$C_3$ alkyl group having a $C_1$–$C_6$ alkylcarbonyloxy group such as formyloxymethyl group, acetoxymethyl group, 1-acetoxyethyl group, 2-acetoxyethyl group, 3-acetoxypropyl group, propionyloxymethyl group, butyryloxymethyl group, and valeryloxymethyl group; a $C_1$–$C_3$ aminoalkyl group such as aminomethyl group, 1-aminoethyl group, 2-aminoethyl group, and 3-aminopropyl group; a monoalkylamino($C_1$–$C_3$ alkyl) group having a $C_1$–$C_8$ alkyl group on the nitrogen atom such as methylaminomethyl group, ethylaminomethyl group, 1-methylaminoethyl group, 2-methylaminoethyl group, and 3-methylaminopropyl group; and a dialkylamino($C_1$–$C_3$ alkyl) group having the same or different $C_1$–$C_8$ alkyl groups on the nitrogen atom such as dimethylaminomethyl group, diethylaminomethyl group, 1-dimethylaminoethyl group, 2-dimethylaminoethyl group, and 3-dimethylaminopropyl group.

Examples of the $C_1$–$C_{18}$ alkyloxy group represented by $R^1$ include, for example, methoxy group, ethoxy group, propoxy group, isopropoxy group, butoxy group, isobutoxy group, sec-butoxy group, tert-butoxy group, pentyloxy group, isopentyloxy group, neopentyloxy group, 1,1-dimethylpropyloxy group, hexyloxy group, isohexyloxy group, heptyloxy group, octyloxy group, nonyloxy group, decyloxy group, undecyloxy group, dodecyloxy group, tridecyloxy group, tetradecyloxy group, pentadecyloxy group, octadecyloxy group and the like. Examples of the $C_3$–$C_{18}$ alkenyloxy group represented by $R^1$ include, for example, allyloxy group, 2-butenyloxy group, 3-butenyloxy group, 2-pentenyloxy group, 3-pentenyloxy group, 4-pentenyloxy group, 2-methyl-2-butenyloxy group, 3-methyl-2-butenyloxy group, 2-hexenyloxy group, 5-hexenyloxy group, 2-heptenyloxy group, 6-heptenyloxy group, 2-octenyloxy group, 7-octenyloxy group, 2-nonenyloxy group, 8-nonenyloxy group and the like. Examples of the $C_3$–$C_{18}$ alkynyloxy group represented by $R^1$ include, for example, propargyloxy group, 2-butynyloxy group, 3-butynyloxy group, 2-pentynyloxy group, 3-pentynyloxy group, 4-pentynyloxy group, 1-methyl-2-pentynyloxy group, 4-methyl-2-pentynyloxy group, 2-hexynyloxy group, 5-hexynyloxy group, 2-heptynyloxy group, 6-heptynyloxy group, 2-octynyloxy group, 7-octynyloxy group and the like. These groups may be substituted with one or more substituents A.

Examples of the $C_3$–$C_8$ cycloalkyloxy group represented by $R^1$ include, for example, cyclopropyloxy group, cyclobutyloxy group, cyclopentyloxy group, cyclohexyloxy group, cycloheptyloxy group, and cyclooctyloxy group, and examples of the $C_6$–$C_{14}$ aryloxy group represented by $R^1$ include, for example, phenoxy group, naphthoxy group, and anthryloxy group. These groups may be substituted with one or more substituents B.

Examples of the heterocyclic group represented by $R^1$ include, for example, residues of heterocyclic rings having 1–4 hetero atoms selected from oxygen atom, sulfur atom, and nitrogen atom, and having total ring-constituting atoms of 5–10, for example, furan ring, dihydrofuran ring, tetrahydrofuran ring, pyran ring, dihydropyran ring, tetrahydropyran ring, benzofuran ring, isobenzofuran ring, chromene ring, chroman ring, isochroman ring, thiophene ring, benzothiophene ring, pyrrole ring, pyrroline ring, pyrrolidine ring, imidazole ring, imidazoline ring, imidazolidine ring, pyrazole ring, pyrazoline ring, pyrazolidine ring, triazole ring, tetrazole ring, pyridine ring, pyridine oxide ring, piperidine ring, pyrazine ring, piperazine ring, pyrimidine ring, pyridazine ring, indolizine ring, indole ring, indoline ring, isoindole ring, isoindoline ring, indazole ring, benzimidazole ring, purine ring, quinolizine ring, quinoline ring, phthalazine ring, naphtylidine ring, quinoxaline ring, quinazoline ring, cinnoline ring, pteridine ring, oxazole ring, oxazolidine ring, isoxazole ring, isoxazolidine ring, thiazole ring, benzothiazole ring, thiazylidine ring, isothiazole ring, isothiazolidine ring, dioxane ring, dithian ring, morpholine ring, thiomorpholine ring, phthalimide ring and the like. The heterocyclic group may have one or more substituents B.

As the optionally substituted $C_1$–$C_{18}$ alkyl group, and as the optionally substituted $C_3$–$C_{18}$ alkenyl group, the optionally substituted $C_3$–$C_{18}$ alkynyl group, the optionally substituted $C_3$–$C_8$ cycloalkyl group, and the optionally substituted $C_6$–$C_{14}$ aryl group which are independently represented by $R^4$ and $R^5$, such as those explained as to $R^1$ may be used. When the symbol "W" represents nitrogen atom, as the optionally substituted $C_1$–$C_{18}$ alkyl that may be present on the nitrogen atom, such as those explained as to $R^1$ may be used.

Examples of the $C_1$–$C_8$ alkyl group represented by $R^2$ include, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, n-heptyl group, n-octyl group and the like, and examples of the $C_3$–$C_8$ alkenyl group represented by $R^2$ include, for example, allyl group, 2-butenyl group, 3-butenyl group, 2pentenyl group, 3-pentenyl group, 4-pentenyl group, 2-methyl-2-butenyl group, 3-methyl-2-butenyl group, 2-hexenyl group, 5-hexenyl group, 2-heptenyl group, 6-heptenyl group, 2-octenyl group, 7-octenyl group and the like. These groups may be have one or more substituents A.

Examples of the $C_1$–$C_8$ alkyloxy group represented by $R^2$ include, for example, methoxy group, ethoxy group, propoxy group, isopropoxy group, butoxy group, isobutoxy group, sec-butoxy group, tert-butoxy group, pentyloxy group, isopentyloxy group, neopentyloxy group, 1,1-dimethylpropyloxy group, hexyloxy group, isohexyloxy group, heptyloxy group, octyloxy group and the like. Examples of the $C_1$–$C_8$ alkylthio group represented by $R^2$ include, for example, methylthio group, ethylthio group, propylthio group, isopropylthio group, butylthio group, isobutylthio group, sec-butylthio group, tert-butylthio group, pentylthio group, isopentylthio group, neopentyl thio group, 1,1-dimethylpropylthio group, hexylthio group, isohexylthio group, heptylthio group, octylthio group and the like. These groups may be have one or more substituents A.

Examples of the $C_1$–$C_8$ alkyloxycarbonyl group represented by $R^2$ include, for example, methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group, isopentyloxycarbonyl group, neopentyloxycarbonyl group, 1,1-dimethylpropyloxycarbonyl group, hexyloxycarbonyl group, isohexyloxycarbonyl group, heptyloxycarbonyl group, octyloxycarbonyl group and the like, and examples of the $C_3$–$C_8$ cycloalkyloxycarbonyl group represented by $R^2$ include, for example, cyclopropyloxycarbonyl group, cyclobutyloxycarbonyl group, cyclopentyloxycarbonyl group, cyclohexyloxycarbonyl group, cycloheptyloxycarbonyl group, cyclooctyloxy carbonyl group and the like. The aforementioned cycloalkyloxycarbonyl groups may have one or more substituents B, and the aforementioned alkyloxycarbonyl groups may have one or more substituents A.

Examples of the $C_1$–$C_8$ alkylaminocarbonyl group represented by $R^2$ include, for example, methylaminocarbonyl group, ethylaminocarbonyl group, propylaminocarbonyl group, isopropylaminocarbonyl group, butylaminocarbonyl group, isobutylaminocarbonyl group, sec-butylaminocarbonyl group, tert-butylaminocarbonyl group, pentylaminocarbonyl group, isopentylaminocarbonyl group, neopentylaminocarbonyl group, 1,1dimethylpropylaminocarbonyl group, hexylaminocarbonyl group, isohexylaminocarbonyl group, heptylaminocarbonyl group, octylaminocarbonyl group and the like. Examples of the $C_1$–$C_8$ dialkylaminocarbonyl group represented by $R^2$ include, for example, dimethylaminocarbonyl group, diethylaminocarbonyl group, dipropylaminocarbonyl group, diisopropylaminocarbonyl group, dibutylaminocarbonyl group, diisobutylaminocarbonyl group, dipentylaminocarbonyl group, diisopentylaminocarbonyl group, dihexylaminocarbonyl group, diisohexylaminocarbonyl group, diheptylaminocarbonyl group, dioctylaminocarbonyl group and the like. These groups may have one or more substituents A.

As the optionally substituted $C_3$–$C_8$ cycloalkyl group, optionally substituted $C_3$–$C_8$ cycloalkyloxy group, and optionally substituted $C_6$–$C_{14}$ aryloxy group represented by $R^2$, such as those explained as to $R^1$ may be used. $R^3$ represents a pyridyl group, which may be any one of 2-pyridyl group, 3-pyridyl group, and 4-pyridyl group. The pyridyl group may have one or more substituents B.

$R^1$ may preferably a $C_1$–$C_{18}$ alkyl group which may be substituted, a $C_3$–$C_{18}$ alkenyl group which may be substituted, a $C_3$–$C_{18}$ alkynyl group which may be substituted, a $C_3$–$C_8$ cycloalkyl group which may be substituted, a $C_6$–$C_{14}$ aryl group which may be substituted, a heterocyclic group which may be substituted by an alkyl group, or a group represented by —N($R^4$)—W—$R^5$ wherein $R^4$ and $R^5$ independently represent a hydrogen atom, a $C_1$–$C_{18}$ alkyl group which may be substituted, a $C_3$–$C_{18}$ alkenyl group which may be substituted, a $C_3$–$C_{18}$ alkynyl group which may be substituted, a $C_3$–$C_8$ cycloalkyl group which may be substituted, or a $C_6$–$C_{14}$ aryl group which may be substituted, and symbol "W" represents a single bond, carbonyl group, sulfonyl group, or a nitrogen atom which may be substituted with a $C_1$–$C_{18}$ alkyl group which may be substituted.

More preferably, $R^1$ may be a $C_1$–$C_{18}$ alkyl group which may be substituted, a $C_3$–$C_8$ cycloalkyl group which may be substituted, a $C_6$–$C_{14}$ aryl group which may be substituted, a heterocyclic group which may be substituted by an unsubstituted alkyl group, or a group represented by —N($R^4$)—W—$R^5$ wherein $R^4$ and $R^5$ independently represent a hydrogen atom, a $C_1$–$C_{18}$ alkyl group, or a substituted $C_6$–$C_{14}$ aryl group which may be substituted, and symbol "W" represents a single bond.

$R^2$ may preferably be hydrogen atom, a $C_1$–$C_8$ alkyl group which may be substituted, a $C_3$–$C_8$ alkenyl group which may be substituted, a $C_3$–$C_8$ cycloalkyl group which may be substituted, a halogen atom, nitro group, cyano group, an amino group which may be substituted, carboxyl group, a $C_1$–$C_8$ alkyloxycarbonyl group which may be substituted, a $C_3$–$C_8$ cycloalkyloxycarbonyl group which may be substituted, carbamoyl group, a $C_1$–$C_8$ alkylaminocarbonyl group which may be substituted, or a $C_1$–$C_8$ dialkylaminocarbonyl group which may be substituted, and more preferably, hydrogen atom, a $C_1$–$C_8$ alkyl group, or a halogen atom, and most preferably hydrogen atom. $R^3$ may preferably be 3-pyridyl group or 4-pyridyl group, and more preferably 4-pyridyl group.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, and L-glucamine; or salts with basic amino acids such as lysine, δ-hydroxylysine, and arginine. When a basic group exists, examples include salts with mineral acids such as hydrochloric acid, hydrobromic acid, sulfuric acid, nitric acid, phosphoric acid; salts with organic acids such as methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, and salicylic acid; or salts with acidic amino acids such as aspartic acid, and glutamic acid.

In addition to the pyrimidone derivatives represented by the aforementioned formula (I) and salts thereof, their solvates and hydrates also fall within the scope of the present invention. The pyrimidone derivatives represented by the aforementioned formula (I) may have one or more asymmetric carbon atoms. As for the stereochemistry of such asymmetric carbon atoms, they may independently be in either (R) and (S) configuration, and the pyrimidone derivatives may exist as stereoisomers such as optical isomers, or diastereoisomers. Any stereoisomers of pure form, any mixtures of stereoisomers, racemates and the like fall within the scope of the present invention. Furthermore, as the pyrimidone derivatives represented by the aforementioned formula (I), a 3H-4-one compound, a 4-hydroxy compound, and a 1H-4-one compound of may exist as tautomers. The existence of such tautomers is readily apparent to those skilled in the art, and these tautomers fall within the scope of the present invention.

Examples of preferred compounds of the present invention are shown in the tables below. However, the scope of the present invention is not limited by the following compounds.

TABLE 1
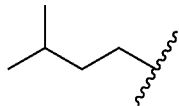
| Compound No. | R¹ | R² | R³ |
|---|---|---|---|
| 1 | Me | H | 4-Py |
| 2 | Et | H | 4-Py |
| 3 | n-Pr | H | 4-Py |
| 4 | i-Pr | H | 4-Py |
| 5 | n-Bu | H | 4-Py |
| 6 | i-Bu | H | 4-Py |
| 7 | sec-Bu | H | 4-Py |
| 8 | tert-Bu | H | 4-Py |
| 9 | n-$C_5H_{11}$ | H | 4-Py |
| 10 | 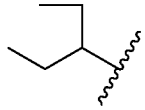 | H | 4-Py |
| 11 | 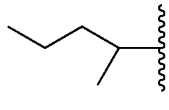 | H | 4-Py |
| 12 |  | H | 4-Py |
| 13 | 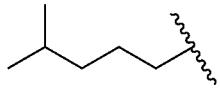 | H | 4-Py |
| 14 | n-$C_6H_{13}$ | H | 4-Py |
| 15 | 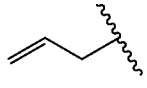 | H | 4-Py |
| 16 | n-$C_7H_{15}$ | H | 4-Py |
| 17 | n-$C_8H_{17}$ | H | 4-Py |
| 18 | n-$C_9H_{19}$ | H | 4-Py |
| 19 | n-$C_{10}H_{21}$ | H | 4-Py |
| 20 | n-$C_{11}H_{23}$ | H | 4-Py |
| 21 | n-$C_{12}H_{25}$ | H | 4-Py |
| 22 | n-$C_{13}H_{27}$ | H | 4-Py |
| 23 | n-$C_{14}H_{29}$ | H | 4-Py |
| 24 | n-$C_{15}H_{31}$ | H | 4-Py |
| 25 | n-$C_{16}H_{33}$ | H | 4-Py |
| 26 | n-$C_{17}H_{35}$ | H | 4-Py |
| 27 | n-$C_{18}H_{37}$ | H | 4-Py |
| 28 | 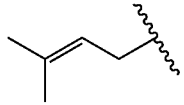 | H | 4-Py |
| 29 |  | H | 4-Py |

TABLE 1-continued
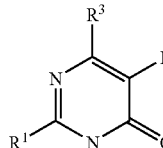
| Compound No. | R¹ | R² | R³ |
|---|---|---|---|
| 30 | 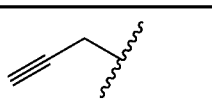 | H | 4-Py |
| 31 | 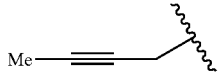 | H | 4-Py |
| 32 | 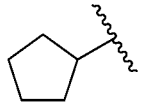 | H | 4-Py |
| 33 | 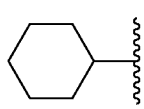 | H | 4-Py |
| 34 | 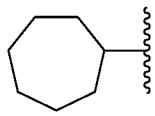 | H | 4-Py |
| 35 | Ph | H | 4-Py |
| 36 | 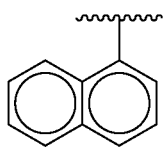 | H | 4-Py |
| 37 | 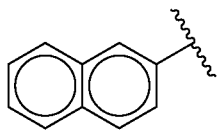 | H | 4-Py |
| 38 | 2-Me—Ph | H | 4-Py |
| 39 | 3-Me—Ph | H | 4-Py |
| 40 | 4-Me—Ph | H | 4-Py |
| 41 | 2-Et—Ph | H | 4-Py |
| 42 | 3-Et—Ph | H | 4-Py |
| 43 | 4-Et—Ph | H | 4-Py |
| 44 | 2-F—Ph | H | 4-Py |
| 45 | 3-F—Ph | H | 4-Py |
| 46 | 4-F—Ph | H | 4-Py |
| 47 | 2-Cl—Ph | H | 4-Py |
| 48 | 3-Cl—Ph | H | 4-Py |
| 49 | 4-Cl—Ph | H | 4-Py |
| 50 | 2-Br—Ph | H | 4-Py |
| 51 | 3-Br—Ph | H | 4-Py |
| 52 | 4-Br—Ph | H | 4-Py |
| 53 | 2-MeO—Ph | H | 4-Py |
| 54 | 3-MeO—Ph | H | 4-Py |
| 55 | 4-MeO—Ph | H | 4-Py |
| 56 | 2-EtO—Ph | H | 4-Py |
| 57 | 3-EtO—Ph | H | 4-Py |
| 58 | 4-EtO—Ph | H | 4-Py |
| 59 | 2-CN—Ph | H | 4-Py |
| 60 | 3-CN—Ph | H | 4-Py |

TABLE 1-continued
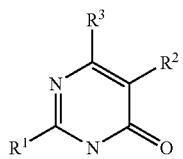
| Compound No. | R¹ | R² | R³ |
|---|---|---|---|
| 61 | 4-CN—Ph | H | 4-Py |
| 62 | 2-NO₂—Ph | H | 4-Py |
| 63 | 3-NO₂—Ph | H | 4-Py |
| 64 | 4-NO₂—Ph | H | 4-Py |
| 65 | 2-CF₃—Ph | H | 4-Py |
| 66 | 3-CF₃—Ph | H | 4-Py |
| 67 | 4-CF₃—Ph | H | 4-Py |
| 68 | 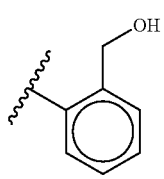 | H | 4-Py |
| 69 | 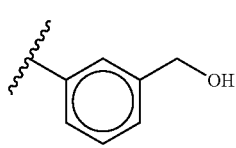 | H | 4-Py |
| 70 | 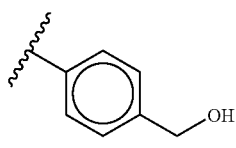 | H | 4-Py |
| 71 | 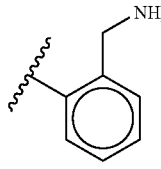 | H | 4-Py |
| 72 | 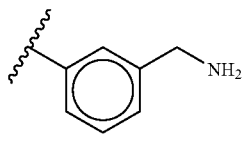 | H | 4-Py |
| 73 | 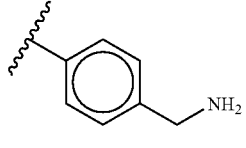 | H | 4-Py |
| 74 | 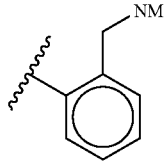 | H | 4-Py |

TABLE 1-continued

[Structure: pyrimidin-4(3H)-one with R¹ at 2-position, R² at 5-position, R³ at 6-position]

| Compound No. | R¹ | R² | R³ |
|---|---|---|---|
| 75 | 3-(NMe₂CH₂)-phenyl | H | 4-Py |
| 76 | 4-(NMe₂CH₂)-phenyl | H | 4-Py |
| 77 | CH(Ph)- | H | 4-Py |
| 78 | 2-Me-benzyl | H | 4-Py |
| 79 | 3-Me-benzyl | H | 4-Py |
| 80 | 4-Me-benzyl | H | 4-Py |
| 81 | 2-OMe-benzyl | H | 4-Py |
| 82 | 3-OMe-benzyl | H | 4-Py |
| 83 | 4-OMe-benzyl | H | 4-Py |
| 84 | 2-Cl-benzyl | H | 4-Py |

TABLE 1-continued
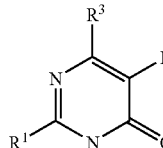
| Compound No. | R¹ | R² | R³ |
|---|---|---|---|
| 85 | 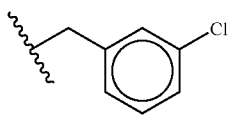 | H | 4-Py |
| 86 | 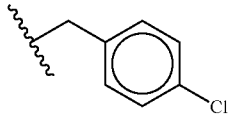 | H | 4-Py |
| 87 | 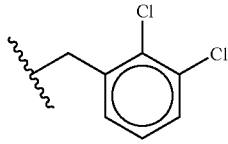 | H | 4-Py |
| 88 | 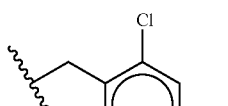 | H | 4-Py |
| 89 | 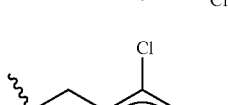 | H | 4-Py |
| 90 | 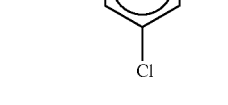 | H | 4-Py |
| 91 | 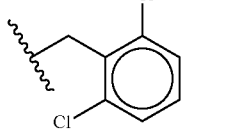 | H | 4-Py |
| 92 | 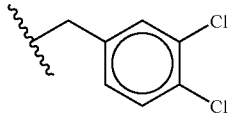 | H | 4-Py |
| 93 | 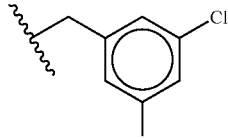 | H | 4-Py |

TABLE 1-continued
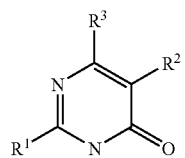
| Compound No. | R¹ | R² | R³ |
|---|---|---|---|
| 94 | Ph-(CH₂)₃- | H | 4-Py |
| 95 | Ph-(CH₂)₅- | H | 4-Py |
| 96 | naphthalen-1-ylmethyl | H | 4-Py |
| 97 | naphthalen-2-ylmethyl | H | 4-Py |
| 98 | -CH₂-CH=CH-Ph | H | 4-Py |
| 99 | -CH₂-C≡C-Ph | H | 4-Py |
| 100 | -CH₂-OH | H | 4-Py |
| 101 | -CH₂-NH₂ | H | 4-Py |
| 102 | -CH₂-NMe₂ | H | 4-Py |
| 103 | -CH₂CH₂-OH | H | 4-Py |
| 104 | -CH₂CH₂-NH₂ | H | 4-Py |
| 105 | -CH₂CH₂-NMe₂ | H | 4-Py |
| 106 | -CH₂CH₂CH₂-OH | H | 4-Py |

TABLE 1-continued

| Compound No. | R¹ | R² | R³ |
|---|---|---|---|
| 107 | ~(CH2)3NH2 | H | 4-Py |
| 108 | ~(CH2)3NMe2 | H | 4-Py |
| 109 | ~(CH2)4OH | H | 4-Py |
| 110 | ~(CH2)4NH2 | H | 4-Py |
| 111 | ~(CH2)4NMe2 | H | 4-Py |
| 112 | MeO— | H | 4-Py |
| 113 | EtO— | H | 4-Py |
| 114 | n-PrO— | H | 4-Py |
| 115 | i-PrO— | H | 4-Py |
| 116 | n-BuO— | H | 4-Py |
| 117 | i-BuO— | H | 4-Py |
| 118 | t-BuO— | H | 4-Py |
| 119 | n-C₅H₁₁O— | H | 4-Py |

TABLE 1-continued
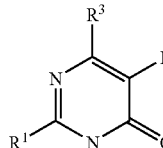
| Compound No. | R¹ | R² | R³ |
|---|---|---|---|
| 120 | n-C₆H₁₃O— | H | 4-Py |
| 121 |  | H | 4-Py |
| 122 | 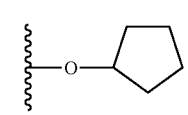 | H | 4-Py |
| 123 | —OPh | H | 4-Py |
| 124 | 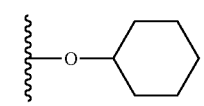 | H | 4-Py |
| 125 |  | H | 4-Py |
| 126 | 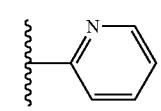 | H | 4-Py |
| 127 | 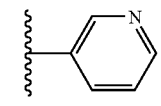 | H | 4-Py |
| 128 | 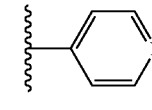 | H | 4-Py |
| 129 | 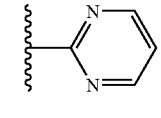 | H | 4-Py |
| 130 | 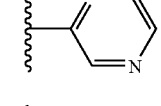 | H | 4-Py |
| 131 | 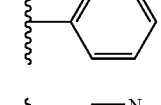 | H | 4-Py |

TABLE 1-continued
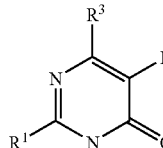
| Compound No. | R¹ | R² | R³ |
|---|---|---|---|
| 132 |  | H | 4-Py |
| 133 | 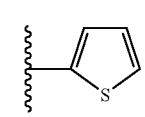 | H | 4-Py |
| 134 | 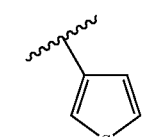 | H | 4-Py |
| 135 | 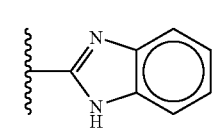 | H | 4-Py |
| 136 | 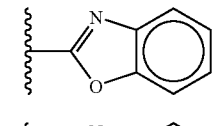 | H | 4-Py |
| 137 | 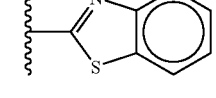 | H | 4-Py |
| 138 | 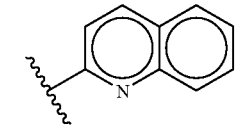 | H | 4-Py |
| 139 | 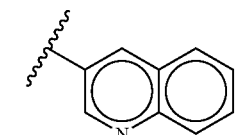 | H | 4-Py |
| 140 | 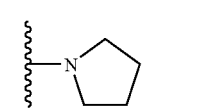 | H | 4-Py |
| 141 | 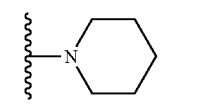 | H | 4-Py |
| 142 | 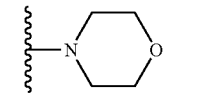 | H | 4-Py |

TABLE 1-continued
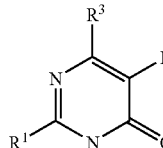
| Compound No. | R¹ | R² | R³ |
| --- | --- | --- | --- |
| 143 | 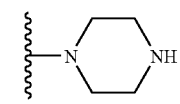 | H | 4-Py |
| 144 | 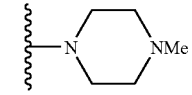 | H | 4-Py |
| 145 | 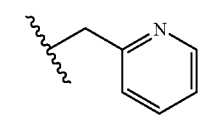 | H | 4-Py |
| 146 | 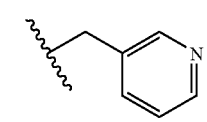 | H | 4-Py |
| 147 | 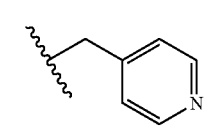 | H | 4-Py |
| 148 | 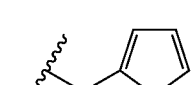 | H | 4-Py |
| 149 |  | H | 4-Py |
| 150 | 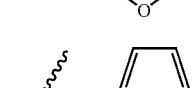 | H | 4-Py |
| 151 | 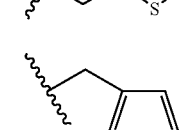 | H | 4-Py |
| 152 | 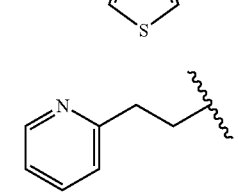 | H | 4-Py |
| 153 | 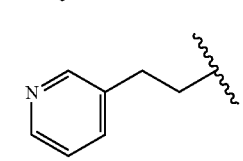 | H | 4-Py |

TABLE 1-continued
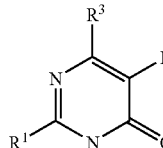
| Compound No. | R¹ | R² | R³ |
|---|---|---|---|
| 154 | 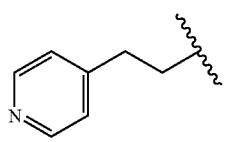 | H | 4-Py |
| 155 | 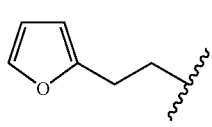 | H | 4-Py |
| 156 | 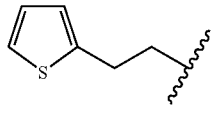 | H | 4-Py |
| 157 | $NH_2$ | H | 4-Py |
| 158 | NHMe | H | 4-Py |
| 159 | NHEt | H | 4-Py |
| 160 | NHn-Pr | H | 4-Py |
| 161 | NHi-Pr | H | 4-Py |
| 162 | NHn-Bu | H | 4-Py |
| 163 | NHi-Bu | H | 4-Py |
| 164 | NHt-Bu | H | 4-Py |
| 165 | NHn-$C_5H_{11}$ | H | 4-Py |
| 166 | NHn-$C_6H_{13}$ | H | 4-Py |
| 167 | 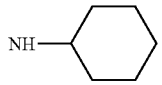 | H | 4-Py |
| 168 | NHPh | H | 4-Py |
| 169 | $NMe_2$ | H | 4-Py |
| 170 | $NEt_2$ | H | 4-Py |
| 171 | Nn-$Pr_2$ | H | 4-Py |
| 172 | $NHNH_2$ | H | 4-Py |
| 173 | NHNHMe | H | 4-Py |
| 174 | $NHNMe_2$ | H | 4-Py |
| 175 | $NMeNH_2$ | H | 4-Py |
| 176 | $NMeNMe_2$ | H | 4-Py |
| 177 | $NHCOCH_3$ | H | 4-Py |
| 178 | $NHCOC_2H_5$ | H | 4-Py |
| 179 | NHCOPh | H | 4-Py |
| 180 | $NHSO_2Me$ | H | 4-Py |
| 181 | $NHSO_2Ph$ | H | 4-Py |
| 182 | 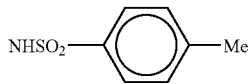 | H | 4-Py |
| 183 | Ph | Me | 4-Py |
| 184 | 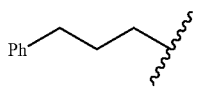 | Me | 4-Py |
| 185 | Ph | Et | 4-Py |

TABLE 1-continued

[Structure: pyrimidin-4(3H)-one with R¹ at 2-position, R² at 5-position, R³ at 6-position]

| Compound No. | R¹ | R² | R³ |
|---|---|---|---|
| 186 | Ph(CH₂)₃– | Et | 4-Py |
| 187 | Ph | n-Pr | 4-Py |
| 188 | Ph(CH₂)₃– | n-Pr | 4-Py |
| 189 | Ph | i-Pr | 4-Py |
| 190 | Ph(CH₂)₃– | i-Pr | 4-Py |
| 191 | Ph | n-Bu | 4-Py |
| 192 | Ph(CH₂)₃– | n-Bu | 4-Py |
| 193 | Ph | i-Bu | 4-Py |
| 194 | Ph(CH₂)₃– | i-Bu | 4-Py |
| 195 | Ph | tBu | 4-Py |
| 196 | Ph(CH₂)₃– | tBu | 4-Py |
| 197 | Ph | n-C₅H₁₁ | 4-Py |
| 198 | Ph(CH₂)₃– | n-C₅H₁₁ | 4-Py |
| 199 | Ph | n-C₆H₁₃ | 4-Py |
| 200 | Ph(CH₂)₃– | n-C₆H₁₃ | 4-Py |
| 201 | Ph | CH₂=CHCH₂CH₂– | 4-Py |
| 202 | Ph(CH₂)₃– | CH₂=CHCH₂CH₂– | 4-Py |

TABLE 1-continued
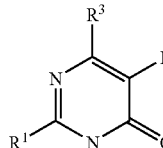
| Compound No. | R¹ | R² | R³ |
|---|---|---|---|
| 203 | Ph | 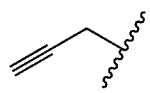 | 4-Py |
| 204 | 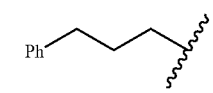 | 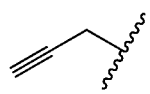 | 4-Py |
| 205 | Ph | 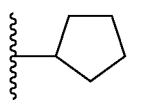 | 4-Py |
| 206 | 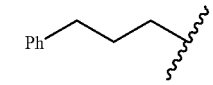 | 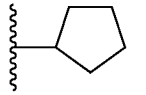 | 4-Py |
| 207 | Ph | 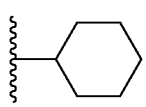 | 4-Py |
| 208 | 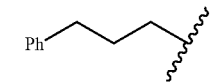 | 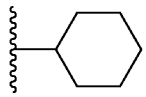 | 4-Py |
| 209 | 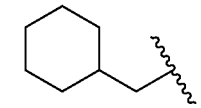 | 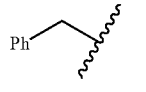 | 4-Py |
| 210 | 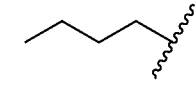 | 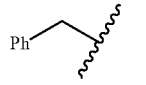 | 4-Py |
| 211 | Me |  | 4-Py |
| 212 | Ph |  | 4-Py |
| 213 | 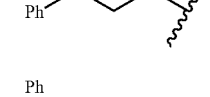 |  | 4-Py |
| 214 | Ph | 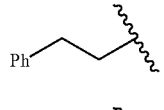 | 4-Py |
| 215 | 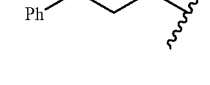 | 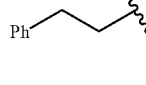 | 4-Py |

TABLE 1-continued
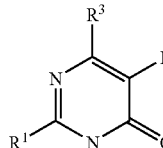
| Compound No. | R¹ | R² | R³ |
|---|---|---|---|
| 216 | Ph |  Ph~~~ | 4-Py |
| 217 | 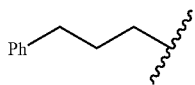 Ph~~~ | 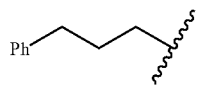 Ph~~~ | 4-Py |
| 218 | Ph | OH | 4-Py |
| 219 |  Ph~~~ | OH | 4-Py |
| 220 | Ph | OMe | 4-Py |
| 221 | 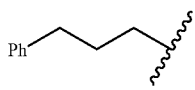 Ph~~~ | OMe | 4-Py |
| 222 | Ph | OEt | 4-Py |
| 223 |  Ph~~~ | OEt | 4-Py |
| 224 | Ph | OPh | 4-Py |
| 225 |  Ph~~~ | OPh | 4-Py |
| 226 | Ph | SMe | 4-Py |
| 227 | 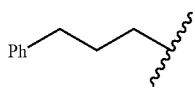 Ph~~~ | SMe | 4-Py |
| 228 | Ph | F | 4-Py |
| 229 |  Ph~~~ | F | 4-Py |
| 230 | Ph | Cl | 4-Py |
| 231 |  Ph~~~ | Cl | 4-Py |
| 232 | NH₂ | Cl | 4-Py |
| 233 | Ph | Br | 4-Py |
| 234 | 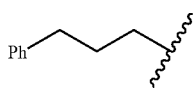 Ph~~~ | Br | 4-Py |

TABLE 1-continued
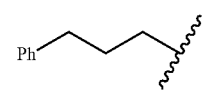
| Compound No. | R¹ | R² | R³ |
| --- | --- | --- | --- |
| 235 | Ph | NO$_2$ | 4-Py |
| 236 | 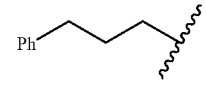 | NO$_2$ | 4-Py |
| 237 | Ph | CN | 4-Py |
| 238 | 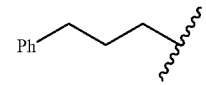 | CN | 4-Py |
| 239 | Ph | NH$_2$ | 4-Py |
| 240 | 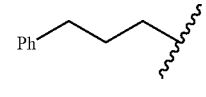 | NH$_2$ | 4-Py |
| 241 | Ph | NMe$_2$ | 4-Py |
| 242 | 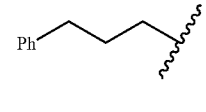 | NMe$_2$ | 4-Py |
| 243 | Ph | —COOH | 4-Py |
| 244 |  | —COOH | 4-Py |
| 245 | Ph | —COOMe | 4-Py |
| 246 |  | —COOMe | 4-Py |
| 247 | Ph | —COOEt | 4-Py |
| 248 | 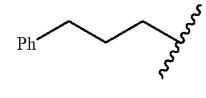 | —COOEt | 4-Py |
| 249 | Ph | CONH$_2$ | 4-Py |
| 250 | 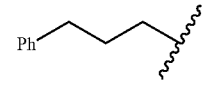 | CONH$_2$ | 4-Py |
| 251 | Ph | CONMe$_2$ | 4-Py |
| 252 |  | CONMe$_2$ | 4-Py |

TABLE 1-continued
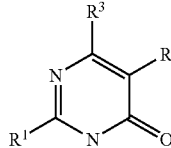
| Compound No. | R¹ | R² | R³ |
|---|---|---|---|
| 253 | Ph | H | 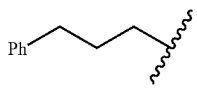 |
| 254 | 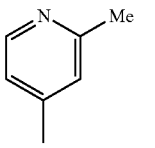 | H | |
| 255 | Ph | H | 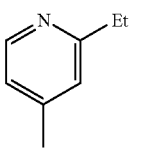 |
| 256 | 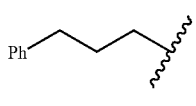 | H | |
| 257 | Ph | H | 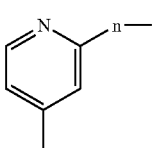 |
| 258 | 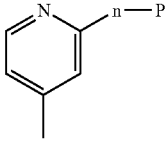 | H | |
| 259 | Ph | H | 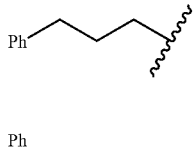 |
| 260 | 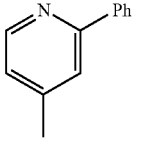 | H | |
| 261 | Ph | H | 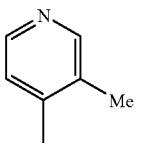 |
| 262 | 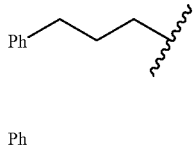 | H | |
| 263 | Ph | H | 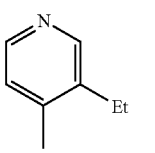 |
| 264 | 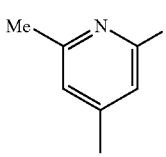 | H | |
| 265 | Ph | H | 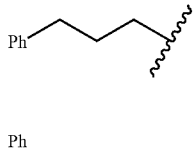 |
| 266 | 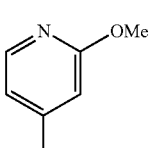 | H | |
| 267 | Ph | H | 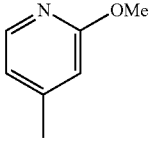 |
| 268 | 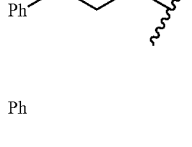 | H | |
| 269 | 4-Py | H | |

TABLE 1-continued
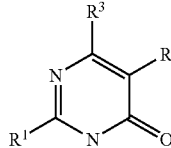
| Compound No. | R¹ | R² | R³ |
|---|---|---|---|
| 270 | Ph | H | 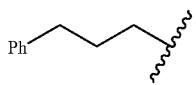 |
| 271 | Ph~~~ | H | |
| 272 | Ph | H | 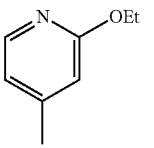 |
| 273 | Ph~~~ | H | |
| 274 | Ph | H | 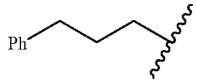 |
| 275 | Ph~~~ | H | |
| 276 | Ph | H | 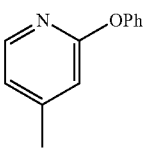 |
| 277 | Ph~~~ | H | |
| 278 | Ph | H | 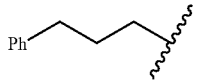 |
| 279 | Ph~~~ | H | |
| 280 | Ph | H | 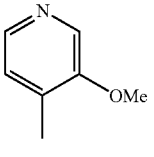 |
| 281 | Ph~~~ | H | |
| 282 | Ph | H | 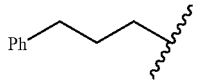 |
| 283 | Ph~~~ | H | |
| 284 | 4-Py | H | |
| 285 | Ph | H | 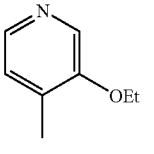 |
| 286 | Ph~~~ | H | |

TABLE 1-continued
| Compound No. | R¹ | R² | R³ |
|---|---|---|---|
| 287 | Ph | H | 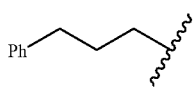 |
| 288 | 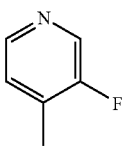 | H | |
| 289 | Ph | H | 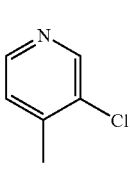 |
| 290 | 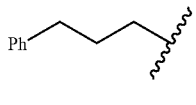 | H | |
| 291 | Ph | H | 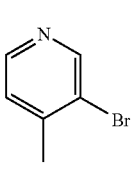 |
| 292 | 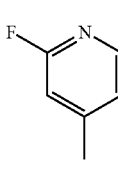 | H | |
| 293 | Ph | H | 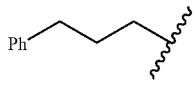 |
| 294 | 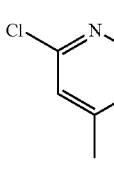 | H | |
| 295 | Ph | H | 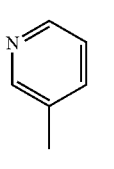 |
| 296 | 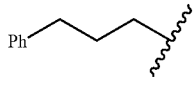 | H | |
| 297 | Me | H | 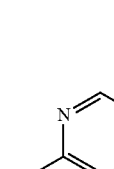 |
| 298 | Ph | H | |
| 299 | 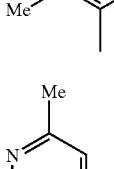 | H | |
| 300 | 4-Py | H | |
| 301 | NMe₂ | H | |
| 302 | Ph | H | 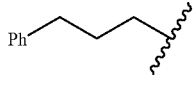 |
| 303 | 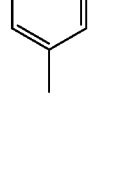 | H | |
| 304 | Ph | H | 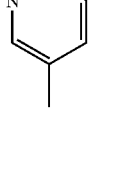 |
| 305 | 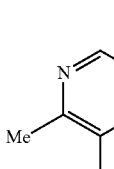 | H | |

TABLE 1-continued
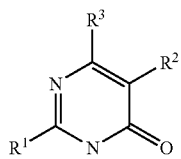
| Compound No. | R¹ | R² | R³ |
|---|---|---|---|
| 306 | Ph | H | 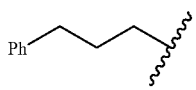 |
| 307 | 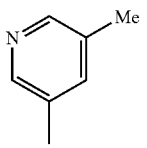 | H | |
| 308 | Ph | H | 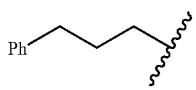 |
| 309 | 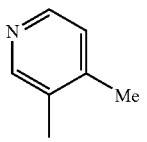 | H | |
| 310 | Ph | H | 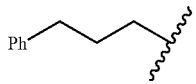 |
| 311 | 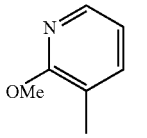 | H | |
| 312 | Ph | H | 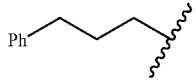 |
| 313 | 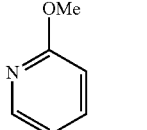 | H | |
| 314 | Ph | H | 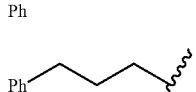 |
| 315 | 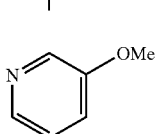 | H | |
| 316 | Ph | H | 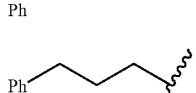 |
| 317 | 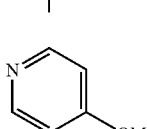 | H | |
| 318 | Ph | H | 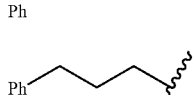 |
| 319 | 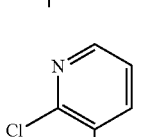 | H | |
| 320 | Ph | H | 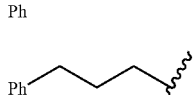 |
| 321 | 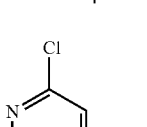 | H | |

TABLE 1-continued

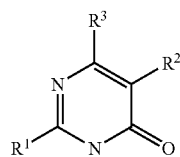

| Compound No. | R¹ | R² | R³ |
|---|---|---|---|
| 322 | Ph | H | 5-chloropyridin-3-yl |
| 323 | Ph(CH₂)₃CH- | H | 5-chloropyridin-3-yl |
| 324 | Ph | H | 4-chloropyridin-3-yl |
| 325 | Ph(CH₂)₃CH- | H | 4-chloropyridin-3-yl |
| 326 | Ph | H | 6-methylpyridin-2-yl |
| 327 | Ph(CH₂)₃CH- | H | 6-methylpyridin-2-yl |
| 328 | Ph | H | 2,6-dimethylpyridin-3-yl |
| 329 | Ph(CH₂)₃CH- | H | 2,6-dimethylpyridin-3-yl |
| 330 | Ph | H | 2,5-dimethylpyridin-4-yl |
| 331 | Ph(CH₂)₃CH- | H | 2,5-dimethylpyridin-4-yl |
| 332 | Ph | H | 2,4-dimethylpyridin-5-yl |
| 333 | Ph(CH₂)₃CH- | H | 2,4-dimethylpyridin-5-yl |
| 334 | Ph | H | 2,3-dimethylpyridin-5-yl |
| 335 | Ph(CH₂)₃CH- | H | 2,3-dimethylpyridin-5-yl |
| 336 | Ph | H | 2-methoxy-6-methylpyridin-3-yl |
| 337 | Ph(CH₂)₃CH- | H | 2-methoxy-6-methylpyridin-3-yl |

TABLE 1-continued

| Compound No. | R¹ | R² | R³ |
|---|---|---|---|
| 338 | Ph | H | 5-OMe-pyridin-2-yl |
| 339 | Ph(CH₂)₃CH(-)- | H | 5-OMe-pyridin-2-yl |
| 340 | Ph | H | 4-OMe-pyridin-2-yl |
| 341 | Ph(CH₂)₃CH(-)- | H | 4-OMe-pyridin-2-yl |
| 342 | Ph | H | 3-OMe-pyridin-2-yl |
| 343 | Ph(CH₂)₃CH(-)- | H | 3-OMe-pyridin-2-yl |
| 344 | Ph | H | 6-Cl-pyridin-2-yl |
| 345 | Ph(CH₂)₃CH(-)- | H | 6-Cl-pyridin-2-yl |
| 346 | Ph | H | 5-Cl-pyridin-2-yl |
| 347 | Ph(CH₂)₃CH(-)- | H | 5-Cl-pyridin-2-yl |
| 348 | Ph | H | 4-Cl-pyridin-2-yl |
| 349 | Ph(CH₂)₃CH(-)- | H | 4-Cl-pyridin-2-yl |
| 350 | Ph | H | 3-Cl-pyridin-2-yl |
| 351 | Ph(CH₂)₃CH(-)- | H | 3-Cl-pyridin-2-yl |
| 352 | 2-n-Pr—Ph | H | 4-Py |
| 353 | 2-i-Pr—Ph | H | 4-Py |
| 354 | 2-n-Bu—Ph | H | 4-Py |
| 355 | 2-i-Bu—Ph | H | 4-Py |
| 356 | 2-sec-Bu—Ph | H | 4-Py |
| 357 | 2-tert-Bu—Ph | H | 4-Py |
| 358 | 2-n-C₅H₁₁—Ph | H | 4-Py |
| 359 | 2-n-C₆H₁₃—Ph | H | 4-Py |
| 360 | 2-Ph—Ph | H | 4-Py |
| 361 | 3-n-Pr—Ph | H | 4-Py |

TABLE 1-continued

[Structure: pyrimidin-4(3H)-one with R¹ at position 2, R² at position 5, R³ at position 6]

| Compound No. | R¹ | R² | R³ |
| --- | --- | --- | --- |
| 362 | 3-i-Pr—Ph | H | 4-Py |
| 363 | 3-n-Bu—Ph | H | 4-Py |
| 364 | 3-i-Bu—Ph | H | 4-Py |
| 365 | 3-sec-Bu—Ph | H | 4-Py |
| 366 | 3-tert-Bu—Ph | H | 4-Py |
| 367 | 3-n-$C_5H_{11}$—Ph | H | 4-Py |
| 368 | 3-n-$C_6H_{13}$—Ph | H | 4-Py |
| 369 | 3-Ph—Ph | H | 4-Py |
| 370 | -CH₂-(3-Et-Ph) | H | 4-Py |
| 371 | -CH₂-(3-n-Pr-Ph) | H | 4-Py |
| 372 | -CH₂-(3-i-Pr-Ph) | H | 4-Py |
| 373 | -CH₂-(3-n-Bu-Ph) | H | 4-Py |
| 374 | -CH₂-(3-i-Bu-Ph) | H | 4-Py |
| 375 | -CH₂-(3-sec-Bu-Ph) | H | 4-Py |
| 376 | -CH₂-(3-tert-Bu-Ph) | H | 4-Py |
| 377 | -CH₂-(3-n-$C_5H_{11}$-Ph) | H | 4-Py |
| 378 | -CH₂-(3-n-$C_6H_{13}$-Ph) | H | 4-Py |

TABLE 1-continued
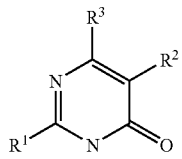
| Compound No. | R¹ | R² | R³ |
|---|---|---|---|
| 379 | 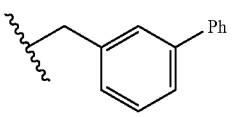 | H | 4-Py |
| 380 | 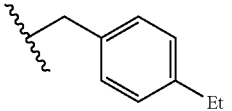 | H | 4-Py |
| 381 | 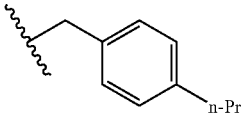 | H | 4-Py |
| 382 | 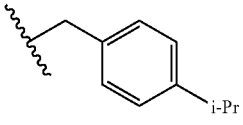 | H | 4-Py |
| 383 | 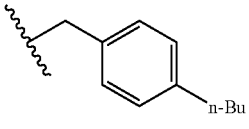 | H | 4-Py |
| 384 | 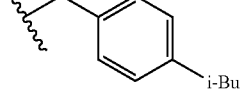 | H | 4-Py |
| 385 | 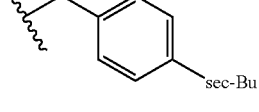 | H | 4-Py |
| 386 | 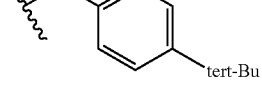 | H | 4-Py |
| 387 | 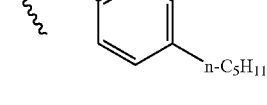 | H | 4-Py |
| 388 | 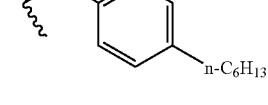 | H | 4-Py |

TABLE 1-continued

![structure: pyrimidinone with R1, R2, R3]

| Compound No. | R¹ | R² | R³ |
|---|---|---|---|
| 389 | 4-biphenylethyl | H | 4-Py |
| 390 | 2-(naphthalen-1-yl)ethyl | H | 4-Py |
| 391 | 3-(naphthalen-1-yl)propyl | H | 4-Py |
| 392 | 2-(naphthalen-2-yl)ethyl | H | 4-Py |
| 393 | 3-(naphthalen-2-yl)propyl | H | 4-Py |
| 394 | CH(Ph)₂ | H | 4-Py |
| 395 | CH₂CH(Ph)₂ | H | 4-Py |
| 396 | CH₂CH₂CH(Ph)₂ | H | 4-Py |
| 397 | HN-CH₂-Ph | H | 4-Py |
| 398 | HN-CH₂CH₂-Ph | H | 4-Py |

TABLE 1-continued
| Compound No. | R¹ | R² | R³ |
|---|---|---|---|
| 399 | 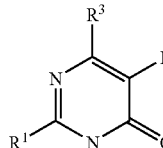 | H | 4-Py |
| 400 | 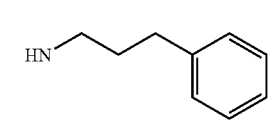 | H | 4-Py |
| 401 | 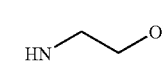 | H | 4-Py |
| 402 | 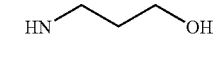 | H | 4-Py |
| 403 | 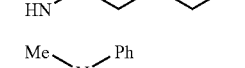 | H | 4-Py |
| 404 | 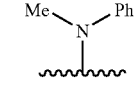 | H | 4-Py |
| 405 | 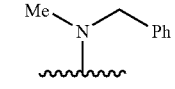 | H | 4-Py |
| 406 | 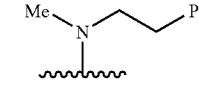 | H | 4-Py |
| 407 | 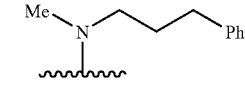 | H | 4-Py |
| 408 | 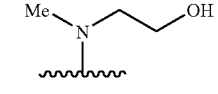 | H | 4-Py |
| 409 | 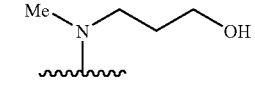 | H | 4-Py |
| 410 | 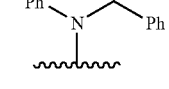 | H | 4-Py |
| 411 | 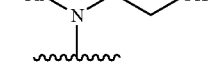 | H | 4-Py |
| 412 | 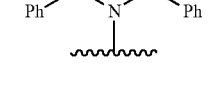 | H | 4-Py |
| 413 |  | H | 4-Py |

TABLE 1-continued
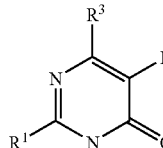
| Compound No. | R¹ | R² | R³ |
|---|---|---|---|
| 414 | 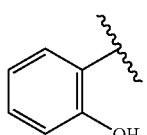 | H | 4-Py |
| 415 | 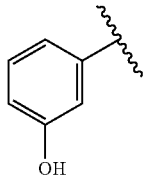 | H | 4-Py |
| 416 | 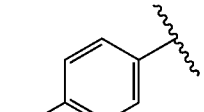 | H | 4-Py |
| 417 | 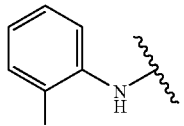 | H | 4-Py |
| 418 | 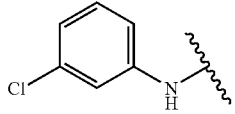 | H | 4-Py |
| 419 | 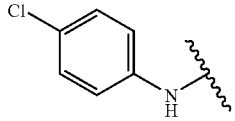 | H | 4-Py |
| 420 | 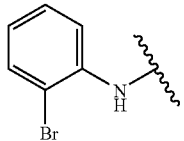 | H | 4-Py |
| 421 | 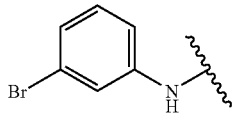 | H | 4-Py |
| 422 | 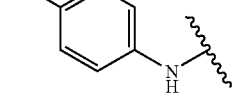 | H | 4-Py |

TABLE 1-continued

| Compound No. | R¹ | R² | R³ |
|---|---|---|---|
| 423 | 2-methylphenyl-NH- | H | 4-Py |
| 424 | 3-methylphenyl-NH- | H | 4-Py |
| 425 | 4-methylphenyl-NH- | H | 4-Py |
| 426 | 2-ethylphenyl-NH- | H | 4-Py |
| 427 | 3-ethylphenyl-NH- | H | 4-Py |
| 428 | 4-ethylphenyl-NH- | H | 4-Py |
| 429 | 2-methoxyphenyl-NH- | H | 4-Py |
| 430 | 3-methoxyphenyl-NH- | H | 4-Py |
| 431 | 4-methoxyphenyl-NH- | H | 4-Py |

TABLE 1-continued

| Compound No. | R¹ | R² | R³ |
|---|---|---|---|
| 432 | 4-ethoxyphenyl-NH- | H | 4-Py |
| 433 | 4-propoxyphenyl-NH- | H | 4-Py |
| 434 | 4-butoxyphenyl-NH- | H | 4-Py |
| 435 | 4-pentyloxyphenyl-NH- | H | 4-Py |
| 436 | cyclohexylmethyl-NH- | H | 4-Py |
| 437 | 2-cyclohexylethyl-NH- | H | 4-Py |
| 438 | 3,3-diphenylpropyl-NH- | H | 4-Py |
| 439 | 3-phenylpropyl-NH- | H | 4-Py |
| 440 | isobutyl(methyl)N- | H | 4-Py |

TABLE 1-continued

![pyrimidone structure with R1, R2, R3 substituents]

| Compound No. | R¹ | R² | R³ |
|---|---|---|---|
| 441 | (isopentyl-NH-) | H | 4-Py |

Particularly preferred compounds of the present invention represented by formula (I) include:

(1) compounds wherein $R^2$ is hydrogen atom, a $C_1$–$C_8$ alkyl group which may be substituted, a $C_3$–$C_8$ alkenyl group which may be substituted, a $C_3$–$C_8$ cycloalkyl group which may be substituted, a halogen atom, nitro group, cyano group, an amino group which may be substituted, carboxyl group, a $C_1$–$C_8$ alkyloxycarbonyl group which may be substituted, a $C_3$–$C_8$ cycloalkyloxycarbonyl group which may be substituted, carbamoyl group, a $C_1$–$C_8$ alkylaminocarbonyl group which may be substituted, or a $C_1$–$C_8$ dialkylaminocarbonyl group which may be substituted;

(2) compounds wherein $R^1$ is a $C_1$–$C_{18}$ alkyl group which may be substituted, a $C_3$–$C_{18}$ alkenyl group which may be substituted, a $C_3$–$C_{18}$ alkynyl group which may be substituted, a $C_3$–$C_8$ cycloalkyl group which may be substituted, a $C_6$–$C_{14}$ aryl group which may be substituted, a heterocyclic group which may be substituted by an alkyl group, or a group represented by —N($R^4$)—W—$R^5$ wherein $R^4$ and $R^5$ independently represent a hydrogen atom, a $C_1$–$C_{18}$ alkyl group which may be substituted, a $C_3$–$C_{18}$ alkenyl group which may be substituted, a $C_3$–$C_{18}$ alkynyl group which may be substituted, a $C_3$–$C_8$ cycloalkyl group which may be substituted, or a $C_6$–$C_{14}$ aryl group which may be substituted, and symbol "W" represents a single bond, carbonyl group, sulfonyl group, or a nitrogen atom which may be substituted with a $C_1$–$C_{18}$ alkyl group which may be substituted;

(3) compounds wherein $R^2$ is hydrogen atom, a $C_1$–$C_8$ alkyl group, or a halogen atom;

(4) compounds wherein $R^1$ is a $C_1$–$C_{18}$ alkyl group which may be substituted, a $C_3$–$C_8$ cycloalkyl group which may be substituted, a $C_6$–$C_{14}$ aryl group which may be substituted, a heterocyclic group which may be substituted by an unsubstituted alkyl group, or a group represented by —N($R^4$)—W—$R^5$ wherein $R^4$ and $R^5$ independently represent a hydrogen atom, a $C_1$–$C_{18}$ alkyl group which may be substituted, or a $C_6$–$C_{14}$ aryl group which may be substituted, and symbol "W" represents a single bond;

(5) compounds wherein $R^2$ is hydrogen atom;

(6) compounds wherein $R^3$ represents a 3-pyridyl group which may be substituted or a 4-pyridyl group which may be substituted; and (7) compounds wherein $R^3$ represents a 4-pyridyl group which may be substituted.

The pyrimidone compounds represented by the aforementioned formula (I) can be prepared, for example, according to the method explained below.

<Preparation Method 1>

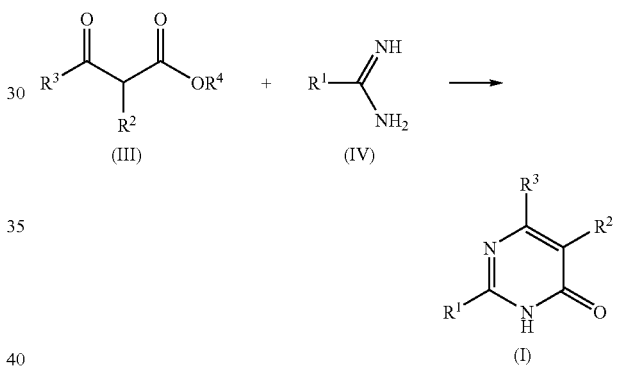

(In the above scheme, $R^4$ represents an alkyl group which may be substituted and definitions of $R^1$–$R^3$ are the same as those already described.)

The 3-ketoester represented by the above formula(III) is allowed to react with the compound represented by formula (IV) or a salt thereof to obtain the compound of the aforementioned formula(I) in the presence of a base such as lithium tert-butoxide, sodium tert-butoxide, potassium tert-butoxide, lithium methoxide, sodium methoxide, potassium methoxide, lithium ethoxide, sodium ethoxide, potassium ethoxide, 1,8-diazabicyclo[5,4,0]undec-7-en, triethylamine, diisopropylethylamine, dimethylbenzylamine, dimethylaniline, diethylaniline and the like. Compounds of formula (III) and formula(IV) are commercially available or may be synthesized according to known methods of one skilled in the art. Compound of formula(I) could be derivatised into other compound of formula(I) using well known method in the art.

Examples of a solvent include, for example, alcoholic solvent such as methanol, ethanol, 1-propanol, isopropanol, tert-butanol; etheric solvents such as diethyl ether, tert-butyl methyl ether, tetrahydrofuran, isopropyl ether; hydrocarbonic solvents such as benzene, toluene, xylene; halogenated solvents such as dichloromethane, chloroform, dichloroethane; aprotic polar solvents such as formamide, N,N- dimethylformamide, N,N-dimethylacetoaminde, N-methylpyrrolidone, dimethyl sulfoxide, sulfolane, hexamethylphosphoric triamide and the like. Generally, a single solvent or a mixture of two or more solvents may be used so as to be suitable to a base used, and the reaction may be carried out for 1 minute to 14 days at a suitable temperature ranging from 0° C. to 250° C. under nitrogen or argon atmosphere or in under ordinary air. In the above reaction, protection or deprotection of a functional group may sometimes be necessary. A suitable protective group can be chosen depending on the type of a functional group, and a method described in the literature may be applied as experimental procedures.

The compounds of the present invention have inhibitory activity against TPK1, and they inhibit TPK1 activity in Alzheimer disease and the like, thereby suppress the neurotoxicity of Aβ and the formation of PHF and inhibit the nerve cell death. Accordingly, the compounds of the present invention are useful as an active ingredient of a medicament which radically enables preventive and/or therapeutic treatment of Alzheimer disease. In addition, the compounds of the present invention are also useful as an active ingredient of a medicament for preventive and/or therapeutic treatment of ischemic cerebrovascular accidents, Down syndrome, cerebral bleeding due to solitary cerebral amyloid angiopathy, progressive supranuclear palsy, subacute sclerosing panencephalitis, postencephalitic parkinsonism, pugilistic encephalosis, Guam parkinsonism-dementia complex, Lewy body disease, Pick's disease, corticobasal degeneration frontotemporal dementia and the like.

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more of pharmaceutical additives. As the active ingredient of the medicament of the present invention, two or more of the aforementioned substance may be used in combination. The above pharmaceutical composition may be supplemented with an active ingredient of other medicament for the treatment of Alzheimer disease and the like. A type of the pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content rations of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

Dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

EXAMPLES

The present invention will be explained more specifically with reference to examples. However, the scope of the present invention is not limited to the following examples. The compound number in the examples corresponds to that in the table above.

Example 1

Preparation of 2-(3-pyridyl)-6-(4-pyridyl)pyrimidin-4-one (Compound 125)

ethyl 3-(4-pyridyl)-3-oxopropionate (0.60 g), 3-amidinopyridine hydrochloride (0.54 g) and potassium carbonate (1.15 g) were added to 5 ml of ethanol, and the mixture was heated under reflux at 75° C. for 20 hours. Acetic acid was added to the reaction mixture, and the solvent was removed by distillation. The residue was added with water and then with acetic acid, and the resulting solid was separated by filtration, washed with water and ethyl acetate, and dried to obtain 0.39 g of the desired compound.

Yield: 50%. Melting Point: >300° C. NMR (DMSO-$d_6$, δ): 7.21 (1H, s), 7.59–7.63 (1H, m), 8.16 (2H, dd, J=1.5, 4.7 Hz), 8.59–8.62 (1H, m), 8.74–8.79 (3H, m), 9.41 (1H, d, J=1.8 Hz).

Compounds of Example 2 to 63 were prepared in a similar manner to that in Example 1. Physical properties of the compounds are shown below.

Example 2

Preparation of 2-methyl-6-(4-pyridyl)pyrimidin-4-one (Compound 1)

Melting Point: >300° C. NMR (DMSO-$d_6$, $\delta$): 2.38 (3H, s), 6.94 (1H, s), 7.98 (2H, dd, J=1.9, 4.5 Hz), 8.69 (2H, dd, J=1.9, 4.6 Hz).

Example 3

Preparation of 2-ethyl-6-(4-pyridyl)pyrimidin-4-one (Compound 2)

Melting Point: 265–269° C. NMR (DMSO-$d_6$, $\delta$): 1.26 (3H, t, J=7.5 Hz), 2.65 (2H, t, J=7.5 Hz), 6.93 (1H, s), 7.99 (2H, dd, J=1.8, 4.6 Hz), 8.69 (2H, dd, J=1.4, 4.6 Hz).

Example 4

Preparation of 2-propyl-6-(4-pyridyl)pyrimidin-4-one (Compound 3)

Melting Point: >300° C. NMR (DMSO-$d_6$, $\delta$): 0.95 (3H, t, J=7.5 Hz), 1.70–1.83 (2H, m), 2.61 (2H, t, J=7.8 Hz), 6.95 (1H, s), 7.99 (2H, dd, J=1.5, 4.8 Hz), 8.70 (2H, dd, J=1.8, 4.8 Hz), 12.64 (1H, bs).

Example 5

Preparation of 2-isopropyl-6-(4-pyridyl)pyrimidin-4-one (Compound 4)

Melting Point: 250–252° C. NMR (DMSO-$d_6$, $\delta$): 1.27 (6H, d, J=7.2 Hz), 2.86–2.95 (1H, m), 6.91 (1H, s), 8.00 (2H, dd, J=1.5, 4.2 Hz), 8.70 (2H, dd, J=1.5, 4.5 Hz).

Example 6

Preparation of 2-butyl-6-(4-pyridyl)pyrimidin-4-one (Compound 5)

Melting Point: 282–285° C. NMR (DMSO-$d_6$, $\delta$): 0.92 (3H, t, J=7.5 Hz), 1.32–1.40 (2H, m), 1.67–1.75 (2H, m), 2.63 (2H, t, J=7.5 Hz), 6.94 (1H, s), 7.98 (2H, dd, J=1.5, 4.8 Hz), 8.70 (2H, dd, J=1.5, 4.2 Hz), 12.59 (1H, bs).

Example 7

Preparation of 2-isobutyl-6-(4-pyridyl)pyrimidin-4-one (Compound 6)

Melting Point: 280–283° C. NMR (DMSO-$d_6$, $\delta$): 0.95 (6H, d, J=6.6 Hz), 2.16–2.25 (1H, m), 2.51 (2H, d, J=7.2 Hz), 6.93 (1H, s), 7.98 (2H, dd, J=1.8, 4.5 Hz), 8.70 (2H, dd, J=1.8, 4.5 Hz), 12.59 (1H, bs).

Example 8

Preparation of 2-pentyl-6-(4-pyridyl)pyrimidin-4-one (Compound 9)

Melting Point: 238–240° C. NMR (DMSO-$d_6$, $\delta$): 0.88 (3H, t, J=6.6 Hz), 1.24–1.38 (4H, m), 1.78–1.90 (2H, m), 2.62 (2H, t, J=7.5 Hz), 6.93 (1H, s), 7.98 (2H, dd, J=1.5, 4.8 Hz), 8.70 (2H, dd, J=1.5, 4.5 Hz).

Example 9

Preparation of 2-hexyl-6-(4-pyridyl)pyrimidin-4-one (Compound 14)

Melting Point: 226–229° C. NMR (DMSO-$d_6$, $\delta$): 0.86 (3H, t, J=6.9 Hz), 1.21–1.38 (6H, m), 1.68–1.78 (2H, m), 2.62 (2H, t, J=7.5 Hz), 6.93 (1H, s), 7.98 (2H, dd, J=1.8, 4.5 Hz), 8.70 (2H, dd, J=1.5, 4.5 Hz), 12.60 (1H, bs).

Example 10

Preparation of 2-heptyl-6-(4-pyridyl)pyrimidin-4-one (Compound 16)

Melting Point: 219–220° C. NMR (DMSO-$d_6$, $\delta$): 0.85 (3H, t, J=6.8 Hz), 1.19–1.37 (8H, m), 1.69–1.78 (2H, m), 2.62 (2H, t, J=7.3 Hz), 6.92 (1H, s), 7.98 (2H, dd, J=1.4, 4.6 Hz), 8.69 (2H, dd, J=1.9, 4.6 Hz).

Example 11

Preparation of 2-octyl-6-(4-pyridyl)pyrimidin-4-one (Compound 17)

Melting Point: 197–200° C. NMR (DMSO-$d_6$, $\delta$): 0.84 (3H, t, J=6.9 Hz), 1.10–1.37 (10H, m), 1.67–1.78 (2H, m), 2.61 (2H, t, J=7.5 Hz), 6.89 (1H, s), 7.98 (2H, dd, J=1.8, 4.5 Hz), 8.68 (2H, dd, J=1.5, 4.5 Hz).

Example 12

Preparation of 2-phenyl-6-(4-pyridyl)pyrimidin-4-one (Compound 35)

Melting Point: >300° C. NMR (DMSO-$d_6$, $\delta$): 7.14 (1H, s), 7.55–7.78 (3H, m), 8.14 (2H, dd, J=1.4, 4.6 Hz), 8.26–8.29 (2H, m), 8.75 (2H, dd, J=1.7, 4.6 Hz).

Example 13

Preparation of 2-(1-naphthyl)-6-(4-pyridyl)pyrimidin-4-one (Compound 36)

Melting Point: >300° C. NMR (DMSO-$d_6$, $\delta$): 7.20 (1H, s), 7.60–7.69 (3H, m), 7.80–7.86 (1H, m), 8.00–8.08 (3H, m), 8.10–8.18 (1H, m), 8.19–8.27 (1H, m), 8.71 (H, dd, J=1.6, 4.4 Hz).

Example 14

Preparation of 6-(4-pyridyl)-2-(2-tolyl)pyrimidin-4-one (Compound 38)

Melting Point: >300° C. NMR (DMSO-$d_6$, $\delta$): 2.44 (3H, s), 7.12 (1H, s), 7.29–7.38 (2H, m), 7.40–7.48 (1H, m), 7.50–7.58 (1H, m), 8.03 (2H, d, J=6.3 Hz), 8.71 (2H, d, J=6.0 Hz), 12.90 (1H, s).

Example 15

Preparation of 6-(4-pyridyl)-2-(3-tolyl)pyrimidin-4-one (Compound 39)

Melting Point: >300° C. NMR (DMSO-$d_6$, δ): 2.42 (3H, s), 7.11 (1H, s), 7.44–7.49 (2H, m), 8.01–8.09 (2H, m), 8.12 (2H, dd, J=1.5, 4.5 Hz), 8.75 (2H, dd, J=1.5, 4.5 Hz).

Example 16

Preparation of 6-(4-pyridyl)-2-(4-tolyl)pyrimidin-4-one (Compound 40)

Melting Point: >300° C. NMR (DMSO-$d_6$, δ): 2.41 (3H, s), 7.08 (1H, s), 7.38 (2H, d, J=8.1 Hz), 8.12 (2H, dd, J=1.5, 4.5 Hz), 8.18 (2H, d, J=8.1 Hz), 8.74 (2H, d, J=4.8 Hz).

Example 17

Preparation of 2-(4-fluorophenyl)-6-(4-pyridyl)pyrimidin-4-one (Compound 46)

Melting Point: >300° C. NMR (DMSO-$d_6$, δ): 7.06 (1H, s), 7.35–7.41 (2H, m), 8.11 (2H, dd, J=1.7, 4.5 Hz), 8.36–8.39 (2H, m), 8.73 (2H, dd, J=1.6, 4.6 Hz).

Example 18

Preparation of 2-(4-chlorophenyl)-6-(4-pyridyl)pyrimidin-4-one (Compound 49)

Melting Point: >300° C. NMR (DMSO-$d_6$, δ): 7.15 (1H, s), 7.63 (2H, d, J=8.7 Hz), 8.13 (2H, dd, J=1.5, 4.5 Hz), 8.31 (2H, d, J=8.7 Hz), 8.75 (2H, d, J=6.0 Hz).

Example 19

Preparation of 2-(3-bromophenyl)-6-(4-pyridyl)pyrimidin-4-one (Compound 51)

Melting Point: 285–287° C. NMR (DMSO-$d_6$, δ): 7.19 (1H, s), 7.52–7.57 (1H, m), 7.81–7.84 (1H, m), 8.14 (2H, dd, J=1.5, 4.5 Hz), 8.28–8.32 (1H, m), 8.42–8.48 (1H, m), 8.75 (2H, dd, J=1.5, 4.8 Hz).

Example 20

Preparation of 2-(3-methoxyphenyl)-6-(4-pyridyl)pyrimidin-4-one (Compound 54)

Melting Point: 262–264° C. NMR (DMSO-$d_6$, δ): 3.87 (3H, s), 7.11 (1H, s), 7.16–7.20 (1H, m), 7.45–7.51 (1H, m), 7.82 (1H, s), 7.87–7.90 (1H, m), 8.12 (2H, dd, J=1.5, 4.5 Hz), 8.74 (2H, dd, J=1.5, 4.5 Hz).

Example 21

Preparation of 2-(3-ethoxyphenyl)-6-(4-pyridyl)pyrimidin-4-one (Compound 57)

Melting Point: 250–253° C. NMR (DMSO-$d_6$, δ): 1.38 (3H, t, J=6.9 Hz), 4.15 (2H, q, J=6.9 Hz), 7.13 (1H, s), 7.15–7.19 (1H, m), 7.44–7.50 (1H, m), 7.80 (1H, s), 7.84–7.88 (1H, m), 8.13 (2H, dd, J=1.5, 4.8 Hz), 8.75 (2H, dd, J=1.5, 4.8 Hz), 12.92 (1H, bs).

Example 22

Preparation of 2-(3-cyanophenyl)-6-(4-pyridyl)pyrimidin-4-one (Compound 60)

Melting Point: >300° C. NMR (DMSO-$d_6$, δ): 7.22 (1H, s), 7.76–7.81 (1H, m), 8.07–8.10 (1H, m), 8.18 (2H, dd, J=1.2, 4.5 Hz), 8.57–8.62 (1H, m), 8.71–8.77 (3H, m).

Example 23

Preparation of 2-(4-cyanophenyl)-6-(4-pyridyl)pyrimidin-4-one (Compound 61)

Melting Point: >300° C. NMR (DMSO-$d_6$, δ): 7.25 (1H, s), 8.06 (2H, d, J=8.4 Hz), 8.16 (2H, dd, J=1.5, 4.5 Hz), 8.47 (2H, d, J=8.4 Hz), 8.76 (2H, d, J=1.5, 4.8 Hz).

Example 24

Preparation of 2-(4-nitrophenyl)-6-(4-pyridyl)pyrimidin-4-one (Compound 64)

Melting Point: >300° C. NMR (DMSO-$d_6$, δ): 7.30 (1H, s), 8.17 (2H, dd, J=1.1, 4.7 Hz), 8.40 (2H, d, J=8.8 Hz), 8.56 (2H, d, J=8.8 Hz), 8.76 (2H, d, J=5.9 Hz).

Example 25

Preparation of 6-(4-pyridyl)-2-(3-trifluorophenyl)-pyrimidin-4-one (Compound 66)

NMR (DMSO-$d_6$, δ): 7.18 (1H, s), 7.78–7.84 (1H, m), 7.95–8.00 (1H, m), 8.13 (2H, dd, J=1.6, 4.5 Hz), 8.60–8.63 (2H, m), 8.76 (2H, dd, J=1.6, 4.5 Hz).

Example 26

Preparation of 6-(4-pyridyl)-2-(4-trifluorophenyl)-pyrimidin-4-one (Compound 67)

Melting Point: >300° C. NMR (DMSO-$d_6$, δ): 7.26 (1H, s), 7.95 (2H, d, J=8.4 Hz), 8.15 (2H, dd, J=1.2, 4.8 Hz), 8.50 (2H, d, J=8.1 Hz), 8.77 (2H, dd, J=0.9, 4.8 Hz), 13.09 (1H, bs).

Example 27

Preparation of 2-(3-(dimethylaminomethyl)phenyl)-6-(4-pyridyl)pyrimidin-4-one dihydrochloride (Compound 75)

Melting Point: 185–190° C. NMR (DMSO-$d_6$, δ): 2.75 (6H, d, J=4.8 Hz), 4.40 (2H, d, J=5.1 Hz), 7.36 (1H, s), 7.68 (1H, t, J=7.8 Hz), 7.85 (1H, d, J=7.8 Hz), 8.33 (1H, d, J=7.8 Hz), 8.51 (1H, s), 8.59 (2H, d, J=6.6 Hz), 8.94 (2H, d, J=6.3 Hz), 10.98 (1H, bs).

Example 28

Preparation of 2-benzyl-6-(4-pyridyl)pyrimidin-4-one (Compound 77)

Melting Point: 290–294° C. NMR (DMSO-$d_6$, δ): 3.96 (2H, s), 6.97 (1H, s), 7.26–7.42 (5H, m), 7.96 (2H, dd, J=1.5, 4.8 Hz), 8.69 (2H, dd, J=1.5, 4.5 Hz), 12.87 (1H, bs).

Example 29

Preparation of 2-(2-methylbenzyl)-6-(4-pyridyl)pyrimidin-4-one (Compound 78)

Melting Point: 260–263° C. NMR (DMSO-$d_6$, δ): 2.39 (3H, s), 3.99 (2H, s), 6.98 (1H, s), 7.10–7.20 (3H, m), 7.21–7.29 (1H, m), 7.89 (2H, dd, J=1.5, 4.5 Hz), 8.67 (2H, dd, J=1.5, 4.5 Hz), 12.83 (1H, bs).

Example 30

Preparation of 2-(3-methylbenzyl)-6-(4-pyridyl)pyrimidin-4-one (Compound 79)

Melting Point: 245–247° C. NMR (DMSO-$d_6$, δ): 2.29 (3H, s), 3.92 (2H, s), 6.97 (1H, s), 7.05–7.09 (1H, m), 7.17–7.26 (3H, m), 7.96 (2H, dd, J=1.8, 4.5 Hz), 8.69 (2H, dd, J=1.5, 4.5 Hz), 12.85 (1H, bs).

Example 31

Preparation of 2-(4-methylbenzyl)-6-(4-pyridyl)pyrimidin-4-one (Compound 80)

Melting Point: 267–270° C. NMR (DMSO-$d_6$, δ): 2.26 (3H, s), 3.91 (2H, s), 6.96 (1H, s), 7.14 (2H, d, J=7.9 Hz), 7.29 (2H, d, J=8.1 Hz), 7.96 (2H, dd, J=1.5, 4.6 Hz), 8.69 (2H, dd, J=1.8, 4.6 Hz).

Example 32

Preparation of 2-(4-methoxybenzyl)-6-(4-pyridyl)pyrimidin-4-one (Compound 83)

Melting Point: 255–257° C. NMR (DMSO-$d_6$, δ): 3.72 (3H, s), 3.88 (2H, s), 6.90 (2H, d, J=11.7 Hz), 6.95 (1H, s), 7.32 (2H, d, J=11.7 Hz), 7.96 (2H, dd, J=1.5, 4.5 Hz), 8.69 (2H, dd, J=1.5, 4.8 Hz), 12.83 (1H, bs).

Example 33

Preparation of 2-(4-chlorobenzyl)-6-(4-pyridyl)pyrimidin-4-one (Compound 86)

Melting Point: 277–280° C. NMR (DMSO-$d_6$, δ): 3.97 (2H, s), 6.96 (1H, s), 7.37–7.41 (1H, m), 7.94 (2H, dd, J=1.6, 4.4 Hz), 8.68 (2H, dd, J=1.6, 4.5 Hz).

Example 34

Preparation of 2-(2,4-dichlorobenzyl)-6-(4-pyridyl)pyrimidin-4-one (Compound 88)

Melting Point: >300° C. NMR (DMSO-$d_6$, δ): 4.14 (2H, s), 7.00 (1H, s), 7.44–7.52 (2H, m), 7.66 (1H, d, J=2.1 Hz), 7.80 (2H, dd, J=1.5, 4.5 Hz), 8.65 (2H, dd, J=1.5, 4.5 Hz), 12.91 (1H, bs).

Example 35

Preparation of 2-(2-phenylethyl)-6-(4-pyridyl)pyrimidin-4-one (Compound 93)

Melting Point: 264–266° C. NMR (DMSO-$d_6$, δ): 2.91–2.97 (2H, m), 3.06–3.11 (2H, m), 6.95 (1H, s), 7.17–7.22 (1H, m), 7.25–7.33 (4H, m), 8.00 (2H, dd, J=1.5, 4.5 Hz), 8.70 (2H, dd, J=1.5, 4.8 Hz).

Example 36

Preparation of 2-(3-phenylpropyl)-6-(4-pyridyl)pyrimidin-4-one (Compound 94)

Melting Point: 238–248° C. NMR (DMSO-$d_6$, δ): 2.01–2.11 (2H, m), 2.63–2.70 (4H, m), 6.94 (1H, s), 7.16–7.32 (4H, m), 7.99 (2H, dd, J=1.5, 4.8 Hz), 8.70 (2H, dd, J=1.5, 4.8 Hz), 12.60 (1H, bs).

Example 37

Preparation of 2-(2-pyridyl)-6-(4-pyridyl)pyrimidin-4-one (Compound 124)

Melting Point: >300° C. NMR (DMSO-$d_6$, δ): 7.22 (1H, s), 7.66–7.71 (1H, m), 8.08–8.18 (3H, m), 8.54–8.59 (1H, m), 8.75–8.80 (3H, m).

Example 38

Preparation of 2,6-di(4-pyridyl)pyrimidin-4-one (Compound 126)

Melting Point: >300° C. NMR (DMSO-$d_6$, δ): 7.29 (1H, s), 8.17 (2H, dd, J=1.4, 4.6 Hz), 8.22 (2H, d, J=6.2 Hz), 8.76 (2H, d, J=6.2 Hz), 8.82 (2H, dd, J=1.6, 4.6 Hz).

Example 39

Preparation of 2-(2-pyrazinyl)-6-(4-pyridyl)pyrimidin-4-one (Compound 128)

Melting Point: >300° C. NMR (DMSO-$d_6$, δ): 6.73 (1H, s), 8.05 (2H, dd, J=1.4, 4.7 Hz), 8.65–8.74 (4H, m), 9.52 (1H, s).

Example 40

Preparation of 6-(4-pyridyl)-2-(2-pyridylmethyl)pyrimidin-4-one (Compound 45)

Melting Point: 249–252° C. NMR (DMSO-$d_6$, δ): 4.19 (2H, s), 7.00 (1H, s), 7.25–7.33 (1H, m), 7.41–7.49 (1H, m), 7.77–7.82 (1H, m), 7.90 (2H, dd, J=1.5, 4.5 Hz), 8.48–8.51 (1H, m), 8.67 (2H, dd, J=1.5, 4.8 Hz), 12.84 (1H, bs).

Example 41

Preparation of 6-(4-pyridyl)-2-(3-pyridylmethyl)pyrimidin-4-one (Compound 146)

Melting Point: 267–269° C. NMR (DMSO-$d_6$, δ): 4.01 (2H, s), 6.94 (1H, s), 7.36–7.42 (1H, m), 7.80–7.85 (1H, m), 7.91 (2H, dd, J=1.7, 4.6 Hz), 8.46–8.50 (1H, m), 8.59–8.62 (1H, m), 8.67 (2H, dd, J=1.4, 4.6 Hz).

Example 42

Preparation of 6-(4-pyridyl)-2-(2-thienylmethyl)pyrimidin-4-one (Compound 150)

Melting Point: 268–270° C. NMR (DMSO-$d_6$, δ): 4.19 (2H, s), 6.98–7.01 (2H, m), 6.99 (1H, s), 7.06–7.07 (1H, m), 7.44 (1H, dd, J=1.2, 5.2 Hz), 7.99 (2H, dd, J=1.5, 4.6 Hz), 8.71 (2H, dd, J=1.7, 4.6 Hz).

Example 43

Preparation of 2-amino-6-(4-pyridyl)pyrimidin-4-one (Compound 157)

Melting Point: >300° C. NMR (DMSO-$d_6$, δ): 6.28 (1H, s), 6.73 (2H, bs), 7.87 (2H, dd, J=1.5, 4.8 Hz), 8.64 (2H, dd, J=1.5, 4.8 Hz), 10.99 (1H, bs).

Example 44

Preparation of 2-dimethylamino-6-(4-pyridyl)pyrimidin-4-one (Compound 169)

Melting Point: >240° C. NMR (DMSO-$d_6$, δ): 3.14 (6H, s), 6.31 (1H, s), 7.94 (2H, dd, J=1.5, 4.8 Hz), 8.67 (2H, dd, J=1.5, 4.8 Hz).

Example 45

Preparation of 5-methyl-2-phenyl-6-(4-pyridyl)pyrimidin-4-one (Compound 183)

Melting Point: >300° C. NMR (DMSO-$d_6$, δ): 2.06 (3H, s), 7.49–7.59 (3H, m), 7.64 (2H, dd, J=1.5, 4.5 Hz), 8.12–8.15 (2H, m), 8.72 (2H, dd, J=1.5, 4.5 Hz), 12.93 (1H, bs).

Example 46

Preparation of 5-methyl-2-(3-phenylpropyl)-6-(4-pyridyl)pyrimidin-4-one (Compound 184)

Melting Point: 141–143° C. NMR (DMSO-$d_6$, δ): 1.93–2.03 (2H, m), 1.95 (3H, s), 2.55–2.66 (4H, m), 7.14–7.30 (5H, m), 7.51 (2H, dd, J=1.5, 4.5 Hz), 8.68 (2H, dd, J=1.5, 4.2 Hz), 12.50 (1H, bs).

Example 47

Preparation of 5-ethyl-2-phenyl-6-(4-pyridyl)pyrimidin-4-one (Compound 185)

Melting Point: >300° C. NMR (DMSO-$d_6$, δ): 1.09 (3H, t, J=7.5 Hz), 2.42 (2H, q, J=7.5 Hz), 7.48–7.59 (5H, m), 8.09–8.12 (2H, m), 8.72 (2H, dd, J=1.5, 4.2 Hz), 12.87 (1H, bs).

Example 48

Preparation of 5-ethyl-2-(3-phenylpropyl)-6-(4-pyridyl)pyrimidin-4-one (Compound 186)

Melting Point: 161–163° C. NMR (DMSO-$d_6$, δ): 1.02 (3H, t, J=7.5 Hz), 1.89–2.01 (2H, m), 2.31 (2H, q, J=7.5 Hz), 2.54–2.66 (4H, m), 7.14–7.29 (5H, m), 7.43 (2H, dd, J=1.2, 4.5 Hz), 8.67 (2H, d, J=1.5, 4.8 Hz), 12.50 (1H, bs).

Example 49

Preparation of 2-phenyl-5-propyl-6-(4-pyridyl)pyrimidin-4-one (Compound 187)

Melting Point: 274–275° C. NMR (DMSO-$d_6$, δ): 0.81 (3H, t, J=7.5 Hz), 1.49 (2H, m), 2.39 (2H, t, J=7.5 Hz), 7.48–7.60 (5H, m), 8.10 (2H, d, J=7.2 Hz), 8.72 (2H, dd, J=1.5, 4.5 Hz), 12.91 (1H, bs).

Example 50

Preparation of 2-(3-phenylpropyl)-5-propyl-6-(4-pyridyl)pyrimidin-4-one (Compound 188)

Melting Point: 148–149° C. NMR (DMSO-$d_6$, δ): 0.76 (3H, t, J=7.5 Hz), 1.14 (2H, m), 1.96 (2H, m), 2.27 (2H, t, J=7.8 Hz), 2.51–2.65 (4H, m), 7.13–7.20 (3H, m), 7.24–7.29 (2H, m), 7.41 (2H, dd, J=1.5, 4.5 Hz), 8.67 (2H, dd, J=1.5, 4.5 Hz), 12.51 (1H, bs).

Example 51

Preparation of 5-butyl-2-phenyl-6-(4-pyridyl)pyrimidin-4-one (Compound 191)

Melting Point: 269–270° C. NMR (DMSO-$d_6$, δ): 0.78 (3H, t, J=7.5 Hz), 1.21 (2H, m), 1.46 (2H, m), 2.42 (2H, t, J=8.7 Hz), 7.48–7.60 (5H, m), 8.11 (2H, d, J=7.2 Hz), 8.71 (2H, dd, J=1.5, 4.5 Hz).

Example 52

Preparation of 5-butyl-2-(3-phenylpropyl)-6-(4-pyridyl)pyrimidin-4-one (Compound 192)

Melting Point: 146–147° C. NMR (DMSO-$d_6$, δ): 0.75 (3H, t, J=7.2 Hz), 1.17 (2H, m), 1.40 (2H, m), 1.96 (2H, m), 2.49 (2H, t, J=7.2 Hz), 2.50–2.65 (4H, m), 7.13–7.20 (3H, m), 7.24–7.29 (2H, m), 7.42 (2H, dd, J=1.5, 4.5 Hz), 8.67 (2H, dd, J=1.5, 4.5 Hz), 12.51 (1H, bs).

Example 53

Preparation of 5-benzyl-2-methyl-6-(4-pyridyl)pyrimidin-4-one (Compound 211)

NMR (DMSO-$d_6$, δ): 2.33 (3H, s), 3.73 (2H, s), 6.91–6.99 (2H, m), 7.11–7.29 (3H, m), 7.35 (2H, d, J=4.5 Hz), 7.62 (2H, d, J=5.7 Hz), 12.68 (1H, bs).

Example 54

Preparation of 5-benzyl-2-phenyl-6-(4-pyridyl)pyrimidin-4-one (Compound 212)

Melting Point: >300° C. NMR (DMSO-$d_6$, δ): 7.04–7.07 (2H, m), 7.15–7.26 (3H, m), 7.48–7.59 (5H, m), 8.13–8.16 (2H, m), 8.67 (2H, d, J=4.8 Hz), 13.02 (1H, bs).

Example 55

Preparation of 6-(2-ethylpyridin-4-yl)-2-(3-phenylpropyl)pyrimidin-4-one (Compound 256)

Melting Point: 139–141° C. NMR (DMSO-$d_6$, δ): 1.26 (3H, t, J=7.5 Hz), 2.06 (2H, m), 2.63–2.70 (4H, m), 2.82 (2H, q, J=7.5 Hz), 6.90 (1H, s), 7.18–7.30 (5H, m), 7.78 (1H, d, J=6.9 Hz), 7.84 (1H, s), 8.58 (1H, d, J=5.1 Hz).

Example 56

Preparation of 6-(2-methoxypyridin-4-yl)-2-(3-phenylpropyl)pyrimidin-4-one (Compound 268)

Melting Point: 179–181° C. NMR (DMSO-d$_6$, δ): 2.09 (2H, m), 2.62–2.67 (4H, m), 3.89 (3H, s), 6.89 (1H, s), 7.12–7.38 (5H, m), 7.41 (1H, s), 8.27 (1H, d, J=5.4 Hz), 12.55 (1H, bs).

Example 57

Preparation of 6-(2-methoxypyridin-4-yl)-2-(4-pyridyl)pyrimidin-4-one (Compound 269)

Melting Point: 273–274° C. NMR (DMSO-d$_6$, δ): 3.93 (3H, s), 7.24 (1H, bs), 7.58 (1H, s), 7.74 (1H, d, J=5.4 Hz), 8.20 (2H, d, J=6.0 Hz), 8.33 (2H, d, J=5.4 Hz), 8.80 (2H, dd, J=1.5, 4.5 Hz).

Example 58

Preparation of 6-(2-chloropyridin-4-yl)-2-(3-phenylpropyl)pyrimidin-4-one (Compound 283)

Melting Point: 177–179° C. NMR (DMSO-d$_6$, δ): 2.06 (2H, m), 2.63–2.70 (4H, m), 7.02 (1H, s), 7.18–7.31 (5H, m), 8.02 (1H, dd, J=1.5, 5.1 Hz), 8.08 (1H, d, J=1.5 Hz), 8.53 (1H, d, J=5.1 Hz), 12.63 (1H, bs).

Example 59

Preparation of 6-(2-chloropyridin-4-yl)-2-(4-pyridyl)pyrimidin-4-one (Compound 284)

Melting Point: 179–181° C. NMR (DMSO-d$_6$, δ): 7.35 (1H, bs), 8.19–8.23 (3H, m), 8.27 (1H, s), 8.59 (1H, d, J=4.8 Hz), 8.81 (2H, dd, J=1.5, 4.5 Hz).

Example 60

Preparation of 2-methyl-6-(3-pyridyl)pyrimidin-4-one (Compound 297)

Melting Point: 261–263° C. NMR (DMSO-d$_6$, δ): 2.38 (3H, s), 6.87 (1H, s), 7.43–7.53 (1H, m), 8.36–8.40 (1H, m), 8.65–8.67 (1H, m), 9.20 (1H, d, J=2.1 Hz), 12.57 (1H, bs).

Example 61

Preparation of 2-phenyl-6-(3-pyridyl)pyrimidin-4-one (Compound 298)

Melting Point: 233–236° C. NMR (DMSO-d$_6$, δ): 7.05 (1H, s), 7.54–7.60 (4H, m), 8.26–8.30 (2H, m), 8.52–8.55 (1H, m), 8.69–8.72 (1H, m), 9.36 (1H, d, J=2.1 Hz).

Example 62

Preparation of 6-(3-pyridyl)-2-(4-pyridyl)pyrimidin-4-one (Compound 300)

Melting Point: >300° C. NMR (DMSO-d$_6$, δ): 7.23 (1H, s), 7.55–7.59 (1H, m), 8.23 (2H, dd, J=1.2, 4.5 Hz), 8.56–8.60 (1H, m), 8.71–8.74 (1H, m), 8.81 (2H, d, J=1.5, 4.8 Hz), 9.39 (1H, d, J=2.1 Hz), 13.03 (1H, bs).

Example 63

Preparation of 2-dimethylamino-6-(3-pyridyl)pyrimidin-4-one (Compound 301)

Melting Point: 263–266° C. NMR (DMSO-d$_6$, δ): 3.14 (6H, s), 6.25 (1H, bs), 7.45–7.50 (1H, m), 8.34–8.37 (1H, m), 8.62–8.65 (1H, m), 9.19 (1H, d, J=1.8 Hz).

Example 64

Preparation of 5-bromo-2-phenyl6-(4-pyridyl)pyrimidin-4-one (Compound 233)

2-Phenyl-6-(4-pyridyl)pyrimidin-4-one (0.61 g) obtained in Example 12 was dissolved in 3 ml of acetic acid, and then the mixture was added with 0.48 g of N-bromosuccinimide and heated at 90° C. for 1 hour. Water was added to the reaction mixture, and solid mass was separated by filtration. The solid was washed with water, acetone, and ethyl acetate, and dried to obtain 0.74 g of the desired compound.

Yield: 93%. Melting Point: >300° C. NMR (DMSO-d$_6$, δ): 7.51–7.65 (3H, m), 7.73 (2H, dd, J=1.5, 4.5 Hz), 8.13 (2H, d, J=7.2 Hz), 8.75 (2H, dd, J=1.5, 4.5 Hz), 13.45 (1H, bs).

Compounds of Example 65 to 98 were prepared in a similar manner to that in Example 1. Physical properties of the compounds are shown below.

Example 65

Preparation of 5-chloro-2-phenyl-6-(4-pyridyl)pyrimidin-4-one (Compound 230)

Melting Point: >300° C. NMR (DMSO-d$_6$, δ): 7.52–7.62 (3H, m), 7.79 (2H, dd, J=1.5, 4.5 Hz), 8.12–8.16 (2H, m), 8.77 (2H, dd, J=1.5, 4.5 Hz), 13.51 (1H, bs).

Example 66

Preparation of 2-amino-5-chloro-6-(4-pyridyl)pyrimidin-4-one (Compound 232)

Melting Point: >300° C. NMR (DMSO-d$_6$, δ): 6.86 (2H, bs), 7.56 (2H, dd, J=1.5, 4.5 Hz), 8.67 (2H, dd, J=1.5, 4.5 Hz), 11.59 (1H, bs).

Example 67

Preparation of 2-benzoylamino-6-(4-pyridyl)pyrimidin-4-one (Compound 179)

Melting Point: 257–259° C. NMR (DMSO-d$_6$, δ): 7.25 (1H, bs), 7.29 (1H, s), 7.62–7.67 (2H, m), 7.80 (1H, t, J=7.5 Hz), 8.02 (2H, dd, J=1.8, 4.5 Hz), 8.12–8.15 (2H, m), 8.75 (2H, dd, J=1.8, 4.5 Hz).

Example 68

Preparation of 2-(2-chlorobenzyl)-6-(4-pyridyl)pyrimidin-4-one (Compound 84)

Melting Point: 264–266° C. NMR (DMSO-$d_6$, δ): 4.14 (2H, s), 7.00 (1H, s), 7.31–7.50 (4H, m), 7.81 (2H, d, J=6.0 Hz), 8.64 (2H, d, J=5.7 Hz), 12.91 (1H, bs).

Example 69

Preparation of 2-(1-piperidino)-6-(4-pyridyl)pyrimidin-4-one (Compound 141)

Melting Point: 267–268° C. NMR (DMSO-$d_6$, δ): 1.50–1.59 (6H, m), 3.67 (4H, m), 6.29 (1H, s), 7.89 (2H, d, J=5.7 Hz), 8.62 (2H, d, J=5.7 Hz).

Example 70

Preparation of 2-(4-methyl-1-piperazino)-6-(4-pyridyl)pyrimidin-4-one (Compound 144)

Melting Point: 275° C. decomposition. NMR (DMSO-$d_6$, δ): 2.77, 2.79 (3H, s), 3.00–3.20 (2H, m), 3.40–3.58 (4H, m), 4.62–4.78 (2H, m), 6.80 (1H, br), 8.45 (2H, d, J=6.6 Hz), 8.92 (2H, d, J=6.6 Hz), 11.28 (1H, br).

Example 71

Preparation of 2-(diethylamino)-6-(4-pyridyl)pyrimidin-4-one (Compound 170)

Melting Point: 199–200° C. NMR (DMSO-$d_6$, δ): 1.15 (6H, t, J=7.0 Hz), 3.60 (4H, q, J=7.0 Hz), 6.32 (1H, s), 7.93 (2H, d, J=5.8 Hz), 8.67 (2H, d, J=5.7 Hz).

Example 72

Preparation of 6-(4-chloro-3-pyridyl)-2-phenylpyrimidin-4-one (Compound 320)

Melting Point: 286–288° C. NMR (DMSO-$d_6$, δ): 7.09 (1H, s), 7.54–7.69 (4H, m), 8.25–8.28 (2H, m), 8.60 (1H, dd, J=2.5, 8.4 Hz), 9.19 (1H, d, J=2.3 Hz).

Example 73

Preparation of 6-(4-chloro-3-pyridyl)-2-(3-phenylpropyl)pyrimidin-4-one (Compound 321)

Melting Point: 194–196° C. NMR (DMSO-$d_6$, δ): 2.01–2.11 (2H, m), 2.62–2.69 (4H, m), 6.89 (1H, s), 7.15–7.31 (5H, m), 7.63 (1H, d, J=8.3 Hz), 8.44 (1H, dd, J=2.5, 8.4 Hz), 9.05 (1H, d, J=2.3 Hz).

Example 74

Preparation of 2-phenyl-6-(2-pyridyl)pyrimidin-4-one (Compound 326)

Melting Point: 268–271° C. NMR (DMSO-$d_6$, δ): 7.22 (1H, s), 7.51–7.61 (4H, m), 7.97–8.03 (1H, m), 8.28–8.36 (2H, m), 8.49 (1H, d, J=7.5 Hz), 8.73 (1H, d, J=4.2 Hz).

Example 75

Preparation of 2-(3-phenylpropyl)-6-(2-pyridyl)pyrimidin-4-one (Compound 327)

Melting Point: 168–170° C. NMR (DMSO-$d_6$, δ): 2.03–2.13 (2H, m), 2.64–2.71 (4H, m), 7.06 (1H, s), 7.17–7.33 (5H, m), 7.49–7.53 (1H, m), 7.94–8.00 (1H, m), 8.29 (1H, d, J=8.1 Hz), 8.69 (1H, d, J=3.9 Hz), 12.55 (1H, bs).

Example 76

Preparation of 2-(3-biphenyl)-6-(4-pyridyl)pyrimidin-4-one (Compound 369)

Melting Point: 296–298° C. NMR (DMSO-$d_6$, δ): 7.10 (1H, s), 7.40–7.47 (1H, m), 7.51–7.56 (2H, m), 7.62–7.70 (1H, m), 7.82–7.85 (2H, m), 7.90–7.93 (1H, m), 8.14 (2H, d, J=5.8 Hz), 8.29–8.34 (1H, m), 8.53 (1H, s), 8.74 (2H, d, J=5.8 Hz).

Example 77

Preparation of 2-(4-propylbenzyl)-6-(4-pyridyl)pyrimidin-4-one (Compound 381)

Melting Point: 249–252° C. NMR (DMSO-$d_6$, δ): 0.87 (3H, t, J=6.9 Hz), 1.52–1.59 (2H, m), 2.52 (2H, t, J=7.2 Hz), 3.91 (2H, s), 6.97 (1H, s), 7.15 (2H, d, J=8.1 Hz), 7.30 (2H, d, J=8.1 Hz), 7.97 (2H, d, J=6.3 Hz), 8.69 (2H, d, J=6.0 Hz), 12.86 (1H, bs).

Example 78

Preparation of 2-(4-butylbenzyl)-6-(4-pyridyl)pyrimidin-4-one (Compound 383)

Melting Point: 241–243° C. NMR (DMSO-$d_6$, δ): 0.87 (3H, t, J=7.2 Hz), 1.24–1.31 (2H, m), 1.47–1.57 (2H, m), 2.53 (2H, t, J=7.5 Hz), 3.91 (2H, s), 6.96 (1H, s), 7.15 (2H, d, J=8.1 Hz), 7.30 (2H, d, J=7.8 Hz), 7.96 (2H, d, J=5.7 Hz), 8.69 (2H, d, J=5.7 Hz), 12.85 (1H, bs).

Example 79

Preparation of 2-(N-benzyl-N-methylamino)-6-(4-pyridyl)pyrimidin-4-one (Compound 404)

Melting Point: 223–224° C. NMR (DMSO-$d_6$, δ): 3.11 (3H, s), 4.92 (2H, s), 6.40 (1H, s), 7.24–7.38 (5H, m), 7.95 (2H, d, J=5.7 Hz), 8.66 (2H, d, J=5.7 Hz), 11.36 (1H, bs).

Example 80

Preparation of 2-benzylamino-6-(4-pyridyl)pyrimidin-4-one (Compound 397)

Melting Point: 230–232° C. NMR (DMSO-$d_6$, δ): 4.61 (d, J=5.7 Hz, 2H), 6.34 (s, 1H), 7.12 (br, 1H), 7.23–7.41 (m, 5H), 7.90 (dd, J=1.5 Hz, 4.5 Hz, 2H), 8.65 (dd, J=1.5 Hz, 4.5 Hz, 2H), 11.02 (br, 1H).

Example 81

Preparation of 2-(3,3-diphenylpropylamino)-6-(4-pyridyl)pyrimidin-4-one (Compound 438)

Melting Point: 227–228° C. NMR (DMSO-$d_6$, δ): 2.33 (m, 2H), 4.04 (t, J=7.5 Hz, 2H), 6.28 (s, 1H), 6.70 (br, 1H), 7.16–7.36 (m, 10H), 7.77 (d, J=6.0 Hz, 2H), 8.64 (dd, J=1.2 Hz, 6.0 Hz, 2H), 10.93 (br, 1H).

Example 82

Preparation of 2-(4-morpholinyl)-6-(4-pyridyl)pyrimidin-4-one (Compound 142)

Melting Point: 285–288° C. NMR (DMSO-$d_6$, δ): 3.70 (m, 8H), 6.44 (br, 1H), 7.95 (d, J=6.0 Hz, 2H), 8.66 (dd, J=1.5 Hz, 6.0 Hz, 2H), 11.44 (br, 1H).

Example 83

Preparation of 2-cyclohexyl-6-(4-pyridyl)pyrimidin-4-one (Compound 33)

Melting Point: >300° C. NMR (DMSO-$d_6$, δ): 1.20–1.40 (m, 3H), 1.55–1.75 (m, 3H), 1.78–1.93 (m, 4H), 2.63 (m, 1H), 2.92 (s, 1H), 7.99 (dd, J=1.5 Hz, 4.8 Hz, 2H), 8.70 (dd, J=1. Hz, 4.8 Hz, 2H), 12.49 (br, 1H).

Example 84

Preparation of 2-(N-isobutyl-N-methylamino)-6-(4-pyridyl)pyrimidin-4-one (Compound 440)

Melting Point: 212–213° C. NMR (DMSO-$d_6$, δ): 0.89 (d, J=6.6 Hz, 6H), 2.06 (m, 1H), 3.12 (s, 3H), 3.46 (d, J=7.2 Hz, 2H), 6.29 (br, 1H), 7.93 (d, J=6.0 Hz, 2H), 8.67 (dd, J=1.5 Hz, 6.0 Hz, 2H), 11.10 (br, 1H).

Example 85

Preparation of 2-dipropylamino-6-(4-pyridyl)pyrimidin-4-one (Compound 171)

Melting Point: 208–209° C. NMR (DMSO-$d_6$, δ): 0.90 (t, J=7.5 Hz, 6H), 1.60 (m, 4H), 3.50 (t, J=7.5 Hz, 4H), 6.30 (br, 1H), 7.92 (d, J=6.0 Hz, 2H), 8.67 (d, J=6.0 Hz, 2H), 11.20 (br, 1H).

Example 86

Preparation of 2-(3-hydroxypropylamino)-6-(4-pyridyl)pyrimidin-4-one (Compound 401)

Melting Point: 217–219° C. NMR (DMSO-$d_6$, δ): 1.73 (m, 2H), 3.44–3.53 (m, 4H), 4.59 (t, J=5.1 Hz, 1H), 6.31 (s, 1H), 6.64 (br, 1H), 7.93 (dd, J=1.5 Hz, 6.0 Hz, 2H), 8.66 (dd, J=1.5 Hz, 6.0 Hz, 2H), 10.94 (br, 1H).

Example 87

Preparation of 2-(1-pyrrolidinyl)-6-(4-pyridyl)pyrimidin-4-one (Compound 140)

Melting Point: >300° C. NMR (DMSO-$d_6$, δ): 1.92 (m, 4H), 3.53 (m, 4H), 6.28 (brs, 1H), 7.94 (dd, J=1.5 Hz, 6.0 Hz, 2H), 8.66 (dd, J=1.5 Hz, 6.0 Hz, 2H), 11.14 (br, 1H).

Example 88

Preparation of 2-cyclohexylmethylamino-6-(4-pyridyl)pyrimidin-4-one (Compound 436)

Melting Point: 203–205° C. NMR (DMSO-$d_6$, δ): 0.80–1.05 (m, 2H), 1.05–1.35 (m, 3H), 1.55–1.80 (m, 6H), 3.25 (m, 2H), 6.30 (s, 1H), 6.65 (br, 1H), 7.91 (dd, J=1.5 Hz, 4.5 Hz, 2H), 8.66 (dd, J=1.5 Hz, 4.5 Hz, 2H), 10.78 (br, 1H).

Example 89

Preparation of 2-(ethylphenylamino)-6-(4-pyridyl)pyrimidin-4-one (Compound 428)

Melting Point: 232–235° C. NMR (DMSO-$d_6$, δ): 1.19 (t, J=7.5 Hz, 3H), 2.59 (q, J=7.5 Hz, 2H), 6.58 (s, 1H), 7.23 (d, J=8.4 Hz, 2H), 7.60 (d, J=8.4 Hz, 2H), 7.95 (d, J=6.0 Hz, 2H), 8.71 (dd, J=1.2 Hz, 6.0 Hz, 2H), 8.89 (br, 1H), 10.91 (br, 1H).

Example 90

Preparation of 2-(butoxyphenylamino)-6-(4-pyridyl)pyrimidin-4-one (Compound 434)

Melting Point: 207–209° C. NMR (DMSO-$d_6$, δ): 0.94 (t, J=7.5 Hz, 3H), 1.42 (m, 2H), 1.70 (m, 2H), 3.96 (t, J=6.6 Hz, 2H), 6.54 (s, 1H), 6.95 (d, J=9.0 Hz, 2H), 7.56 (d, J=9.0 Hz, 2H), 7.92 (d, J=6.0 Hz, 2H), 8.69 (d, J=6.0 Hz, 2H), 8.85 (br, 1H), 10.93 (br, 1H).

Example 91

Preparation of 2-(bromophenylamino)-6-(4-pyridyl)pyrimidin-4-one (Compound 421)

Melting Point: 289–291° C. NMR (DMSO-$d_6$, δ): 6.69 (br, 1H), 7.23 (m, 1H), 7.33 (t, J=8.1 Hz, 1H), 7.65 (m, 1H), 7.96 (d, J=5.7 Hz, 2H), 8.15 (s, 1H), 8.72 (d, J=5.7 Hz, 2H). m.p.: 289–291° C.

Example 92

Preparation of 2-phenylamino-6-(4-pyridyl)pyrimidin-4-one (Compound 168)

Melting Point: 252–253° C. NMR (DMSO-$d_6$, δ): 6.62 (s, 1H), 7.08 (t, J=7.8 Hz, 1H), 7.39 (d, J=7.8 Hz, 2H), 7.71 (d, J=7.8 Hz, 2H), 7.95 (d, J=6.0 Hz, 2H), 8.71 (d, J=6.0 Hz, 2H), 9.00 (br, 1H), 10.95 (br, 1H).

Example 93

Preparation of 2-(3-methoxyphenylamino)-6-(4-pyridyl)pyrimidin-4-one (Compound 430)

Melting Point: 155° C. NMR (DMSO-d$_6$, δ): 3.79 (s, 3H), 6.59–6.65 (m, 2H), 7.05–7.30 (m, 3H), 7.54 (s, 1H), 7.96 (d, J=5.7 Hz, 2H), 8.71 (d, J=5.7 Hz, 2H).

Example 94

Preparation of 2-(3,3-diphenylpropyl)-6-(4-pyridyl)pyrimidin-4-one (Compound 396)

Melting Point: 297–299° C. NMR (DMSO-d$_6$, δ): 2.49–2.55 (m, 4H), 4.05 (m, 1H), 6.86 (s, 1H), 7.10–7.20 (m, 2H), 7.26–7.37 (m, 8H), 7.97 (dd, J=1.5 Hz, 4.5 Hz, 2H), 8.69 (dd, J=1.5 Hz, 4.5 Hz, 2H).

Example 95

Preparation of 2-(2-naphthylmethyl)-6-(4-pyridyl)pyrimidin-4-one (Compound 97)

Melting Point: >300° C. NMR (DMSO-d$_6$, δ): 4.15 (s, 2H), 6.99 (s, 1H), 7.48–7.52 (m, 2H), 7.58 (d, J=10.2 Hz, 1H), 7.87–7.92 (m, 4H), 7.96 (dd, J=1.5 Hz, 4.5 Hz, 2H), 8.68 (dd, J=1.5 Hz, 4.5 Hz, 2H), 12.96 (br, 1H).

Example 96

Preparation of 2-(3-phenylbenzyl)-6-(4-pyridyl)pyrimidin-4-one (Compound 379)

Melting Point: 234–237° C. NMR (DMSO-d$_6$, δ): 4.05 (s, 2H), 6.99 (s, 1H), 7.37–7.56 (m, 6H), 7.67 (dd, J=1.2 Hz, 6.0 Hz, 2H), 7.74 (s, 1H), 7.98 (dd, J=1.5 Hz, 4.5 Hz, 2H), 8.68 (dd, J=1.5 Hz, 4.5 Hz, 2H), 12.91 (br, 1H).

Example 97

Preparation of 2-(4-hydroxyphenyl)-6-(4-pyridyl)pyrimidin-4-one (Compound 416)

Melting Point: >300° C. NMR (DMSO-d$_6$, δ): 6.87 (d, J=8.7 Hz, 2H), 6.96 (s, 1H), 8.05–8.14 (m, 4H), 8.69 (dd, J=1.5 Hz, 6.0 Hz, 2H), 10.25 (br, 1H), 12.66 (br, 1H).

Test Example: Inhibitory Activity of the Medicament of the Present Invention Against P-GS1 Phosphorylation by Bovine Cerebral TPK1

A mixture containing 100 mM MES-sodium hydroxide (pH 6.5), 1 mM magnesium acetate, 0.5 mM EGTA, 5 mM β-mercaptoethanol, 0.02% Tween 20, 10% glycerol, 12 μg/ml P-GS1, 41.7 μM [γ-$^{32}$P] ATP (68 kBq/ml), bovine cerebral TPK1 and a compound shown in Table (a final mixture contained 1.7% DMSO deriving from a solution of a test compound prepared in the presence of 10% DMSO) was used as a reaction system. The phosphorylation was started by adding ATP, and the reaction was conducted at 25° C. for 2 hours, and then stopped by adding 21% perchloric acid on ice cooling. The reaction mixture was centrifuged at 12,000 rpm for 5 minutes and adsorbed on P81 paper (Whatmann), and then the paper was washed four times with 75 mM phosphoric acid, three times with water and once with acetone. The paper was dried, and the residual radioactivity was measured using a liquid scintillation counter. The results are shown in the table below. The test compound markedly inhibited the P-GS1 phosphorylation by TPK1. The results strongly suggest that the medicaments of the present invention inhibit the TPK1 activity, thereby suppress the Aβ neurotoxicity and the PHF formation, and that the medicaments of the present invention are effective for preventive and/or therapeutic treatment of Alzheimer disease and the above-mentioned diseases.

TABLE 2

| Example | (Compound No.) | IC$_{50}$ (μM) |
|---|---|---|
| 1 | (125) | 2.3 |
| 2 | (1) | 3.0 |
| 5 | (4) | 2.1 |
| 6 | (5) | 1.3 |
| 7 | (6) | 2.4 |
| 12 | (35) | 1.8 |
| 14 | (38) | 4.0 |
| 15 | (39) | 2.2 |
| 16 | (40) | 4.8 |
| 19 | (51) | 8.7 |
| 22 | (60) | 6.2 |
| 24 | (64) | 5.3 |
| 27 | (75) | 3.3 |
| 28 | (77) | 1.3 |
| 29 | (78) | 1.4 |
| 31 | (80) | 2.9 |
| 33 | (86) | 5.5 |
| 35 | (93) | 8.9 |
| 36 | (94) | 0.50 |
| 37 | (124) | 3.8 |
| 38 | (126) | 1.8 |
| 42 | (150) | 7.6 |
| 43 | (157) | 5.7 |
| 44 | (169) | 3.7 |
| 68 | (84) | 1.3 |
| 69 | (141) | 2.5 |
| 71 | (170) | 1.1 |
| 79 | (404) | 2.8 |
| 80 | (397) | 1.1 |
| 82 | (142) | 4.3 |
| 83 | (33) | 2.8 |
| 84 | (440) | 1.1 |
| 85 | (171) | 0.96 |
| 86 | (401) | 10 |
| 87 | (140) | 2.6 |
| 88 | (436) | 1.4 |
| 89 | (428) | 2.3 |
| 90 | (434) | 6.3 |
| 91 | (421) | 1.6 |
| 92 | (168) | 1.6 |
| 93 | (430) | 1.8 |
| 96 | (379) | 0.77 |
| 97 | (416) | 1.7 |

Formulation Example (1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| Compound of Example 1 | 30 mg |
| --- | --- |
| Olive oil | 300 mg |
| Lecithin | 20 mg |

(3) Parenteral Preparations

The ingredients below were mixed by an ordinary method to prepare injections contained in a 1 ml ample.

| Compound of Example 27 | 3 mg |
| --- | --- |
| Sodium chloride | 4 mg |
| Distilled water for infection | 1 ml |

INDUSTRIAL APPLICABILITY

The compounds of the present invention have TPK1 inhibitory activity and are useful as an active ingredient of a medicament for preventive and/or therapeutic treatment of diseases caused by abnormal advance of TPK1 such as Alzheimer disease.

The invention claimed is:

1. A pyrimidone compound represented by formula (I) or a pharmaceutically acceptable salt thereof:

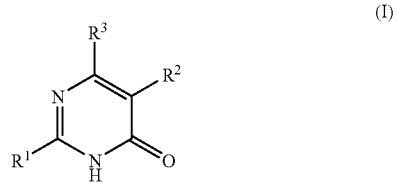

wherein
  $R^1$ represents a group represented by —N($R^4$)—W—$R^5$ wherein
    $R^4$ represents a hydrogen atom;
    $R^5$ represents a $C_1$–$C_{18}$ alkyl group which may be substituted, a $C_3$–$C_{18}$ alkenyl group which may be substituted, a $C_3$–$C_{18}$ alkynyl group which may be substituted, a $C_3$–$C_8$ cycloalkyl group which may be substituted, or a $C_6$–$C_{14}$ aryl group which may be substituted, and
    symbol "W" represents a single bond, a carbonyl group, a sulfonyl group, NH or a nitrogen atom substituted with a $C_1$–$C_{18}$ alkyl group which may be substituted;
  $R^2$ represents a hydrogen atom; and
  $R^3$ represents a 4-pyridyl group which may be substituted.

2. The pyrimidone compound or the pharmaceutically acceptable salt thereof according to claim 1 wherein $R^5$ represents a $C_1$–$C_{18}$ alkyl group substituted with a $C_6$–$C_{10}$ aryl.

3. The pyrimidone compound or the pharmaceutically acceptable salt thereof according to claim 1 wherein $R^2$ represents a hydrogen atom.

4. The pyrimidone compound or the pharmaceutically acceptable salt thereof according to claim 1 wherein the symbol "W" represents a single bond or a carbonyl group.

5. The pyrimidone compound or the pharmaceutically acceptable salt thereof according to claim 4 wherein the symbol "W" represents a single bond.

6. A pyrimidone compound represented by formula (I) or a pharmaceutically acceptable salt thereof:

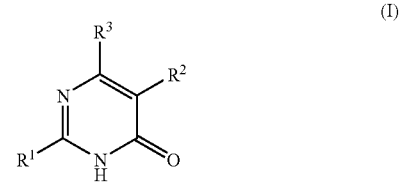

wherein $R^1$ represents a group represented by —N($R^4$)—W—$R^5$ wherein
  $R^4$ represents a hydrogen atom, a $C_1$–$C_{18}$ alkyl group which may be substituted, a $C_3$–$C_{18}$ alkenyl group which may be substituted, a $C_3$–$C_{18}$ alkynyl group which may be substituted, a $C_3$–$C_8$ cycloalkyl group which may be substituted, or a $C_6$–$C_{14}$ aryl group which may be substituted,
  $R^5$ represents an alkyl group which may be substituted, said alkyl group being one of ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, a linear or branched heptyl group, octyl group, nonyl group, decyl group, undecyl group, dodecyl group, tridecyl group, tetradecyl group, pentadecyl group or octadecyl group, a $C_3$–$C_{18}$ alkenyl group which may be substituted, a $C_3$–$C_{18}$ alkynyl group which may be substituted, a $C_3$–$C_8$ cycloalkyl group which may be substituted, or a $C_6$–$C_{14}$ aryl group which may be substituted, and
  symbol "W" represents a single bond, a carbonyl group, a sulfonyl group, NH or a nitrogen atom substituted with a $C_1$–$C_{18}$ alkyl group which may be substituted;
$R^2$ represents a hydrogen atom or a halogen atom; and
$R^3$ represents a 4-pyridyl group which may be substituted.

7. The pyrimidone compound or the pharmaceutically acceptable salt thereof according to claim 6 wherein $R^2$ represents a hydrogen atom.

8. The pyrimidone compound or the pharmaceutically acceptable salt thereof according to claim 6 wherein the symbol "W" represents a single bond or a carbonyl group.

9. The pyrimidone compound or the pharmaceutically acceptable salt thereof according to claim 8 wherein the symbol "W" represents a single bond.

10. The pyrimidone compound or a pharmaceutically acceptable salt thereof according to claim 6 wherein $R^1$ represents N,N-diethylamino group, N,N-dipropylamino group, N-benzyl-N-methylamino group, N-isobutyl-N-methylamino group, N-benzylamino group, N-(3-hydroxypropyl)amino group, N-cyclohexylmethylamino group, N-phenylamino group, N-(4-ethylphenyl)amino group, N-(3-bromophenyl)amino group of N-(3-methoxyphenyl)amino group.

11. A pyrimidone compound which is selected from the group consisting of:
  2-(N-phenylamino)-6-(4-pyridyl)pyrimidin-4-one,
  2-(N,N-diethylamino)-6-(4-pyridyl)pyrimidin-4-one,
  2-(N,N-dipropylamino)-6-(4-pyridyl)pyrimidin-4-one, 2-(N-benzylamino)-6-(4-pyridyl)pyrimidin-4-one,
2-(N-benzyl-N-methylamino)-6-(4-pyridyl)pyrimidin-4-one,
2-(N-(3-bromophenyl)amino)-6-(4-pyridyl)pyrimidin-4-one,
2-(N-(4-ethylphenyl)amino)-6-(4-pyridyl)pyrimidin-4-one,
2-(N-(3-methoxyphenyl)amino)-6-(4-pyridyl)pyrimidin-4-one,
2-(N-cyclohexylmethylamino)-6-(4-pyridyl)pyrimidin-4-one, and
2-(N-isobutyl-N-methylamino)-6-(4pyridyl)pyrimidin-4-one,
or a pharmaceutically acceptable salt thereof.

12. A pharmaceutical composition comprising as an active ingredient a substance selected from the pyrimidone compound or a pharmaceutically acceptable salt thereof according to claim 1.

13. A pharmaceutical composition comprising as an active ingredient a substance selected from the pyrimidone compound or a pharmaceutically acceptable salt thereof according to claim 6.

14. A method for therapeutic treatment of Alzheimer disease, which comprises administering to a patient a therapeutically effective amount of a substance selected from a pyrimidone compound represented by formula (I) or a pharmaceutically acceptable salt thereof:

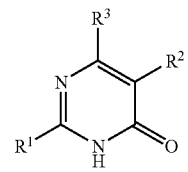

(I)

wherein
$R^1$ represents a group represented by —N($R^4$)—W—$R^5$
wherein
$R^4$ and $R^5$ independently represent a hydrogen atom, a $C_1$–$C_{18}$ alkyl group which may be substituted, a $C_3$–$C_{18}$ alkenyl group which may be substituted, a $C_3$–$C_{18}$ alkynyl group which may be substituted, a $C_3$–$C_8$ cycloalkyl group which may be substituted, or a $C_6$–$C_{14}$ aryl group which may be substituted, and
symbol "W" represents a single bond, a carbonyl group, a sulfonyl group, NH or a nitrogen atom substituted with a $C_1$–$C_{18}$ alkyl group which may be substituted;
$R^2$ represents a hydrogen atom or a halogen atom; and
$R^3$ represents a pyridyl group which may be substituted.

* * * * *